(12) United States Patent
Robertson et al.

(10) Patent No.: US 10,010,504 B2
(45) Date of Patent: Jul. 3, 2018

(54) COMPOSITIONS AND METHODS INCLUDING CELECOXIB AND PLUMBAGIN RELATING TO TREATMENT OF CANCER

(71) Applicant: The Penn State Research Foundation

(72) Inventors: Gavin P. Robertson, Hummelstown, PA (US); Chandagalu D. Raghavendra Gowda, Hershey, PA (US); Arati K. Sharma, Hummelstown, PA (US); Gregory Kardos, Phoenixville, PA (US); Sanjay Singh, Gujarat (IN)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 14/777,160

(22) PCT Filed: Mar. 15, 2013

(86) PCT No.: PCT/US2013/032439
§ 371 (c)(1),
(2) Date: Sep. 15, 2015

(87) PCT Pub. No.: WO2014/143031
PCT Pub. Date: Sep. 18, 2014

(65) Prior Publication Data
US 2016/0045437 A1    Feb. 18, 2016

(51) Int. Cl.
*A61K 31/122* (2006.01)
*A61K 31/415* (2006.01)
*A61K 9/127* (2006.01)
*A61K 45/06* (2006.01)
*A61K 9/14* (2006.01)
*G01N 33/574* (2006.01)

(52) U.S. Cl.
CPC .............. *A61K 9/1271* (2013.01); *A61K 9/14* (2013.01); *A61K 31/122* (2013.01); *A61K 31/415* (2013.01); *A61K 45/06* (2013.01); *G01N 33/57496* (2013.01); *G01N 2333/4703* (2013.01); *G01N 2333/90216* (2013.01)

(58) Field of Classification Search
None
See application file for complete search history.

(56) References Cited

U.S. PATENT DOCUMENTS

| | | | | |
|---|---|---|---|---|
| 4,737,323 A | * | 4/1988 | Martin | A61K 9/1277 210/500.23 |
| 2003/0129224 A1 | * | 7/2003 | Tardi | A61K 9/1278 424/450 |
| 2005/0267189 A1 | * | 12/2005 | Gao | A61K 9/2013 514/406 |
| 2012/0082659 A1 | * | 4/2012 | Land | A61K 31/00 424/130.1 |

FOREIGN PATENT DOCUMENTS

| WO | WO-2000/069434 | | 11/2000 |
|---|---|---|---|
| WO | WO-2012-018948 | * | 2/2012 |
| WO | WO-2012/018948 | | 2/2012 |
| WO | WO-2012-075291 | * | 6/2012 |
| WO | WO-2012-131052 | * | 10/2012 |

OTHER PUBLICATIONS

Wang, C. et al., Plumbagin induces cell cycle arrest and apoptosis through reactive oxygen species/c-Jun N-terminal kinase pathways in human melanoma A375.S2 cells, *Cancer Letters*, 259(1): 82-98, Nov. 19, 2007.

* cited by examiner

*Primary Examiner* — Celeste A Roney
(74) *Attorney, Agent, or Firm* — Dinsmore & Shohl LLP

(57) ABSTRACT

The present invention relates to compositions and methods for treatment of proliferative disease. In specific aspects, the present invention relates to compositions including celecoxib and plumbagin in combination; methods for treatment of a proliferative disease including administration of celecoxib and plumbagin in a subject in need thereof; and particularly methods for treatment of skin cancer including administration of celecoxib and plumbagin in a subject in need thereof.

16 Claims, 27 Drawing Sheets

Size and Zeta potential of nanoliposomes

|  | In water | | In saline | |
|---|---|---|---|---|
|  | Size | Charge | Size | Charge |
| Empty liposome | 66.21 ± 7.30 | -58.1 ± 9.1 | 70.31 ± 3.84 | -0.85 ± 0.23 |
| Celecoxib liposome | 69.73 ± 5.32 | -56.7 ± 6.0 | 74.07 ± 4.11 | -1.03 ± 0.40 |
| Plumbagin liposome | 76.41 ± 9.22 | -64.3 ± 6.3 | 68.22 ± 4.84 | -1.77 ± 0.11 |
| CelePlum-777 | 81.55 ± 8.75 | -60.5 ± 7.4 | 70.64 ± 2.75 | -1.13 ± 0.39 |

COMPOSITIONS AND METHODS INCLUDING CELECOXIB AND PLUMBAGIN RELATING TO TREATMENT OF CANCER

GRANT REFERENCE

This invention was made with government support under Grant Nos. CA127892, CA136667 and CA138634, awarded by the National Institutes of Health. The Government has certain rights in the invention.

FIELD OF THE INVENTION

The present invention relates to compositions and methods for treatment of proliferative disease. In specific aspects, the present invention relates to compositions including celecoxib and plumbagin in combination; methods for treatment of a proliferative disease including administration of celecoxib and plumbagin in a subject in need thereof; and particularly methods for treatment of skin cancer including administration of celecoxib and plumbagin in a subject in need thereof.

BACKGROUND OF THE INVENTION

In spite of recent medical progress, cancer continues to be one of the most common and deadly diseases. Elucidation of biochemical pathways involved in development and progression of various cancers is important to identify potential anti-cancer treatments as well as to develop agents effective to regulate such pathways in other aspects of health and disease.

A particular cancer, melanoma, is the most deadly form of skin cancer due to its high metastatic potential. The COX-2 (cyclooxygenase-2) and STAT3 pathways are abnormally and constitutively activated in up to 70% of melanomas. Cyclins are key to the functioning of the cyclin-cyclin dependent kinase complex in melanoma cells. Compositions and methods are required to inhibit cyclins and the COX-2 and STAT3 pathways and inhibit abnormal cell survival and proliferation.

There is a continuing need for compositions and methods to treat cancer.

SUMMARY OF THE INVENTION

Pharmaceutical compositions are provided according to aspects of the present invention which include plumbagin; celecoxib; and a pharmaceutically acceptable carrier.

Pharmaceutical compositions are provided according to aspects of the present invention which include plumbagin and celecoxib contained together in liposomes.

Pharmaceutical compositions are provided according to aspects of the present invention which include plumbagin and celecoxib contained together in liposomes, wherein the liposomes have an average particle size in the range of 1 nm-500 nm.

Pharmaceutical compositions are provided according to aspects of the present invention which include plumbagin and celecoxib contained together in liposomes, wherein the liposomes have an average particle size in the range of 20 nm-250 nm.

Pharmaceutical compositions are provided according to aspects of the present invention which include plumbagin and celecoxib contained together in liposomes, wherein the liposomes have an average particle size in the range of 50 nm-150 nm.

Pharmaceutical compositions are provided according to aspects of the present invention which include plumbagin and celecoxib contained together in liposomes, wherein the ratio of plumbagin:celecoxib is in the range of 1:100-100:1 and wherein the liposomes have an average particle size in the range of 1 nm-500 nm, 20 nm-250 nm or 50 nm-150 nm.

Pharmaceutical compositions are provided according to aspects of the present invention which include plumbagin and celecoxib contained together in liposomes, wherein the ratio of plumbagin:celecoxib is in the range of 1:50-50:1 and wherein the liposomes have an average particle size in the range of 1 nm-500 nm, 20 nm-250 nm or 50 nm-150 nm.

Pharmaceutical compositions are provided according to aspects of the present invention which include plumbagin and celecoxib contained together in liposomes, wherein the ratio of plumbagin:celecoxib is in the range of 1:1-1:50 and wherein the liposomes have an average particle size in the range of 1 nm-500 nm, 20 nm-250 nm or 50 nm-150 nm.

Pharmaceutical compositions are provided according to aspects of the present invention which include plumbagin and celecoxib contained together in liposomes, wherein the ratio of plumbagin:celecoxib is in the range of 1:10-1:20 and wherein the liposomes have an average particle size in the range of 1 nm-500 nm, 20 nm-250 nm or 50 nm-150 nm.

Pharmaceutical compositions are provided according to aspects of the present invention which include plumbagin and celecoxib contained together in liposomes, wherein the plumbagin is present in a concentration in the range of 0.1 micromolar-100 millimolar and the celecoxib is present in a concentration in the range of 0.1 micromolar-100 millimolar and wherein the liposomes have an average particle size in the range of 1 nm-500 nm, 20 nm-250 nm or 50 nm-150 nm.

Pharmaceutical compositions are provided according to aspects of the present invention which include plumbagin and celecoxib contained together in liposomes, wherein the plumbagin is present in a concentration in the range of 0.5 micromolar-10 millimolar and the celecoxib is present in a concentration in the range of 0.5 micromolar-10 millimolar and wherein the liposomes have an average particle size in the range of 1 nm-500 nm, 20 nm-250 nm or 50 nm-150 nm.

Pharmaceutical compositions are provided according to aspects of the present invention which include plumbagin and celecoxib contained together in liposomes, wherein the plumbagin is present in a concentration in the range of 0.75 micromolar-1 millimolar and the celecoxib is present in a concentration in the range of 0.75 micromolar-1 millimolar and wherein the liposomes have an average particle size in the range of 1 nm-500 nm, 20 nm-250 nm or 50 nm-150 nm.

Pharmaceutical compositions are provided according to aspects of the present invention which include plumbagin and celecoxib contained together in liposomes, wherein the plumbagin is present in a concentration in the range of 1 micromolar-100 micromolar and the celecoxib is present in a concentration in the range of 1 micromolar-100 micromolar and wherein the liposomes have an average particle size in the range of 1 nm-500 nm, 20 nm-250 nm or 50 nm-150 nm.

Pharmaceutical compositions are provided according to aspects of the present invention which include plumbagin and celecoxib contained together in liposomes, wherein the plumbagin is present in a concentration in the range of 0.1 micromolar-50 micromolar and the celecoxib is present in a concentration in the range of 2.5 micromolar-1250 micromolar and wherein the liposomes have an average particle size in the range of 1 nm-500 nm, 20 nm-250 nm or 50 nm-150 nm.

Pharmaceutical compositions are provided according to aspects of the present invention which include celecoxib contained in liposomes.

Pharmaceutical compositions are provided according to aspects of the present invention which include celecoxib contained in liposomes and wherein the liposomes have an average particle size in the range of 1 nm-500 nm, 20 nm-250 nm or 50 nm-150 nm.

Pharmaceutical compositions are provided according to aspects of the present invention which include celecoxib contained in liposomes, wherein the liposomes have an average particle size in the range of 1 nm-500 nm, 20 nm-250 nm or 50 nm-150 nm and wherein the celecoxib is present in a concentration in the range of 0.1 micromolar-100 millimolar.

Pharmaceutical compositions are provided according to aspects of the present invention which include celecoxib contained in liposomes, wherein the liposomes have an average particle size in the range of 1 nm-500 nm, 20 nm-250 nm or 50 nm-150 nm and wherein the celecoxib is present in a concentration in the range of 0.5 micromolar-10 millimolar.

Pharmaceutical compositions are provided according to aspects of the present invention which include celecoxib contained in liposomes, wherein the liposomes have an average particle size in the range of 1 nm-500 nm, 20 nm-250 nm or 50 nm-150 nm and wherein the celecoxib is present in a concentration in the range of 0.75 micromolar-1 millimolar.

Pharmaceutical compositions are provided according to aspects of the present invention which include celecoxib contained in liposomes, wherein the liposomes have an average particle size in the range of 1 nm-500 nm, 20 nm-250 nm or 50 nm-150 nm and wherein the celecoxib is present in a concentration in the range of 1 micromolar-100 micromolar.

Pharmaceutical compositions are provided according to aspects of the present invention which include celecoxib contained in liposomes, wherein the liposomes have an average particle size in the range of 1 nm-500 nm, 20 nm-250 nm or 50 nm-150 nm and wherein the celecoxib is present in a concentration in the range of 2.5 micromolar-1250 micromolar.

Pharmaceutical compositions are provided according to the present invention which include liposomes containing plumbagin, liposomes containing celecoxib, or liposomes containing both plumbagin and celecoxib, wherein the liposomes include at least one polyethylene glycol modified neutral lipid, wherein the amount of polyethylene glycol modified neutral lipid is an amount in the range of 2.5-30 molar percent, inclusive, of total lipids in the liposomes; and one or more anionic, cationic or neutral lipids in an amount in the range of 70-97.5, inclusive, molar percent of total lipids in the liposomes.

Pharmaceutical compositions are provided according to the present invention which include liposomes containing plumbagin, liposomes containing celecoxib, or liposomes containing both plumbagin and celecoxib, wherein the liposomes include at least one polyethylene glycol modified neutral lipid, wherein the amount of polyethylene glycol modified neutral lipid is an amount in the range of 5-20 molar percent, inclusive, of total lipids in the liposomes; and one or more anionic, cationic or neutral lipids in an amount in the range of 80-95, inclusive, molar percent of total lipids in the liposomes.

Pharmaceutical compositions are provided according to the present invention which include liposomes containing plumbagin, liposomes containing celecoxib, or liposomes containing both plumbagin and celecoxib, wherein the liposomes include 1,2-dipalmitoyl-sn-glycero-3-phosphoethanolamine-N-[methoxy(polyethyl glycol)-200], wherein the amount of 1,2-dipalmitoyl-sn-glycero-3-phosphoethanolamine-N-[methoxy(polyethyl glycol)-200] is in the range of 2.5-30 molar percent, inclusive, of total lipids in the liposomes; and L-alpha-phosphatidylcholine in an amount in the range of 70-97.5, inclusive, molar percent of total lipids in the liposomes.

Pharmaceutical compositions are provided according to the present invention which include liposomes containing plumbagin, liposomes containing celecoxib, or liposomes containing both plumbagin and celecoxib, wherein the liposomes include 1,2-dipalmitoyl-sn-glycero-3-phosphoethanolamine-N-[methoxy(polyethyl glycol)-200], wherein the amount of 1,2-dipalmitoyl-sn-glycero-3-phosphoethanolamine-N-[methoxy(polyethyl glycol)-200] is in the range of 5-20 molar percent, inclusive, of total lipids in the liposomes; and L-alpha-phosphatidylcholine in an amount in the range of 80-95, inclusive, molar percent of total lipids in the liposomes.

Methods of treating cancer in a subject in need thereof are provided according to aspects of the present invention which include administering, concurrently or sequentially, a therapeutically effective amount of plumbagin and celecoxib to the subject.

Methods of treating cancer in a subject in need thereof are provided according to aspects of the present invention which include administering, concurrently, a therapeutically effective amount of plumbagin and celecoxib to the subject.

Methods of treating cancer in a subject in need thereof are provided according to aspects of the present invention which include administering, sequentially, a therapeutically effective amount of plumbagin and celecoxib to the subject.

Methods of treating cancer in a subject in need thereof are provided according to aspects of the present invention which include administering a pharmaceutical composition including a therapeutically effective amount of plumbagin and celecoxib to the subject, wherein the plumbagin and celecoxib are administered together in a single formulation.

Methods of treating cancer in a subject in need thereof are provided according to aspects of the present invention which include administering a pharmaceutical composition including a therapeutically effective amount of plumbagin and celecoxib to the subject, wherein the plumbagin and celecoxib are contained together in liposomes.

Methods of treating cancer in a subject in need thereof are provided according to aspects of the present invention which include administering a pharmaceutical composition including a therapeutically effective amount of plumbagin and celecoxib to the subject, wherein the plumbagin and celecoxib are contained together in liposomes, and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of plumbagin and celecoxib to the subject, wherein the plumbagin and celecoxib are contained together in liposomes, wherein the plumbagin is present in a concentration in the range of 0.1 micromolar-100 millimolar and the celecoxib is present in a concentration in the range of 0.1 micromolar-100 millimolar, and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of plumbagin and celecoxib to the subject, wherein the plumbagin and celecoxib are contained together in liposomes, wherein the plumbagin is present in a concentration in the range of 0.5 micromolar-10 millimolar and the celecoxib is present in a concentration in the range of 0.5 micromolar-10 millimolar, and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of plumbagin and celecoxib to the subject, wherein the plumbagin and celecoxib are contained together in liposomes, wherein the plumbagin is present in a concentration in the range of 0.75 micromolar-1 millimolar and the celecoxib is present in a concentration in the range of 0.75 micromolar-1 millimolar and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of plumbagin and celecoxib to the subject, wherein the plumbagin and celecoxib are contained together in liposomes, wherein the plumbagin is present in a concentration in the range of 1 micromolar-100 micromolar and the celecoxib is present in a concentration in the range of 1 micromolar-100 micromolar, and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of plumbagin and celecoxib to the subject, wherein the plumbagin and celecoxib are contained together in liposomes, wherein the plumbagin is present in a concentration in the range of 0.1 micromolar-50 micromolar and the celecoxib is present in a concentration in the range of 2.5 micromolar-1250 micromolar, and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of plumbagin and celecoxib to the subject, wherein the plumbagin and celecoxib are contained together in liposomes, wherein the ratio of plumbagin:celecoxib is in the range of 1:100-100:1 and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of plumbagin and celecoxib to the subject, wherein the plumbagin and celecoxib are contained together in liposomes, wherein the ratio of plumbagin:celecoxib is in the range of 1:50-50:1 and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of plumbagin and celecoxib to the subject, wherein the plumbagin and celecoxib are contained together in liposomes, wherein the ratio of plumbagin:celecoxib is in the range of 1:1-1:50 and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of plumbagin and celecoxib to the subject, wherein the plumbagin and celecoxib are contained together in liposomes, wherein the ratio of plumbagin:celecoxib is in the range of 1:10-1:20 and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of plumbagin and celecoxib to the subject, wherein the plumbagin is contained in liposomes without celecoxib, celecoxib is contained in liposomes without plumbagin or both celecoxib and plumbagin are separately contained in liposomes, and wherein the plumbagin and/or celecoxib are administered concurrently or sequentially.

Methods of treating cancer in a subject in need thereof are provided according to aspects of the present invention which include administering a pharmaceutical composition including a therapeutically effective amount of plumbagin and celecoxib to the subject, wherein the plumbagin is contained in liposomes without celecoxib, celecoxib is contained in liposomes without plumbagin or both celecoxib and plumbagin are separately contained in liposomes, and wherein the liposomes containing plumbagin without celecoxib and liposomes containing celecoxib without plumbagin have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of plumbagin and celecoxib to the subject, wherein the plumbagin is contained in liposomes without celecoxib, celecoxib is contained in liposomes without plumbagin or both celecoxib and plumbagin are separately contained in liposomes, wherein the plumbagin and/or celecoxib are administered concurrently or sequentially, and wherein the ratio of plumbagin:celecoxib administered is in the range of 1:100-100:1.

Methods of treating cancer in a subject in need thereof are provided according to aspects of the present invention which include administering a pharmaceutical composition including a therapeutically effective amount of plumbagin and celecoxib to the subject, wherein the plumbagin is contained in liposomes without celecoxib, celecoxib is contained in liposomes without plumbagin or both celecoxib and plumbagin are separately contained in liposomes, wherein the plumbagin and/or celecoxib are administered concurrently or sequentially, and wherein the ratio of plumbagin:celecoxib administered is in the range of 1:50-50:1.

Methods of treating cancer in a subject in need thereof are provided according to aspects of the present invention which include administering a pharmaceutical composition including a therapeutically effective amount of plumbagin and celecoxib to the subject, wherein the plumbagin is contained in liposomes without celecoxib, celecoxib is contained in liposomes without plumbagin or both celecoxib and plumbagin are separately contained in liposomes, wherein the plumbagin and/or celecoxib are administered concurrently or sequentially, and wherein the ratio of plumbagin:celecoxib administered is in the range of 1:1-1:50.

Methods of treating cancer in a subject in need thereof are provided according to aspects of the present invention which include administering a pharmaceutical composition including a therapeutically effective amount of plumbagin and celecoxib to the subject, wherein the plumbagin is contained in liposomes without celecoxib, celecoxib is contained in liposomes without plumbagin or both celecoxib and plumbagin are separately contained in liposomes, wherein the plumbagin and/or celecoxib are administered concurrently or sequentially, and wherein the ratio of plumbagin:celecoxib administered is in the range of 1:10-1:20.

Methods of treating cancer in a subject in need thereof are provided according to aspects of the present invention which include administering a pharmaceutical composition including a therapeutically effective amount of plumbagin and celecoxib to the subject, wherein the plumbagin is contained in liposomes without celecoxib, celecoxib is contained in liposomes without plumbagin or both celecoxib and plumbagin are separately contained in liposomes, wherein the plumbagin and/or celecoxib are administered concurrently or sequentially, and wherein the plumbagin is administered in a concentration in the range of 0.1 micromolar-100 millimolar and the celecoxib is administered in a concentration in the range of 0.1 micromolar-100 millimolar.

Methods of treating cancer in a subject in need thereof are provided according to aspects of the present invention which include administering a pharmaceutical composition including a therapeutically effective amount of plumbagin and celecoxib to the subject, wherein the plumbagin is contained in liposomes without celecoxib, celecoxib is contained in liposomes without plumbagin or both celecoxib and plumbagin are separately contained in liposomes, wherein the plumbagin and/or celecoxib are administered concurrently or sequentially, and wherein the plumbagin is present in a concentration in the range of 0.5 micromolar-10 millimolar and the celecoxib is present in a concentration in the range of 0.5 micromolar-10 millimolar.

Methods of treating cancer in a subject in need thereof are provided according to aspects of the present invention which include administering a pharmaceutical composition including a therapeutically effective amount of plumbagin and celecoxib to the subject, wherein the plumbagin is contained in liposomes without celecoxib, celecoxib is contained in liposomes without plumbagin or both celecoxib and plumbagin are separately contained in liposomes, wherein the plumbagin and/or celecoxib are administered concurrently or sequentially, and wherein the plumbagin is present in a concentration in the range of 0.75 micromolar-1 millimolar and the celecoxib is present in a concentration in the range of 0.75 micromolar-1 millimolar.

Methods of treating cancer in a subject in need thereof are provided according to aspects of the present invention which include administering a pharmaceutical composition including a therapeutically effective amount of plumbagin and celecoxib to the subject, wherein the plumbagin is contained in liposomes without celecoxib, celecoxib is contained in liposomes without plumbagin or both celecoxib and plumbagin are separately contained in liposomes, wherein the plumbagin and/or celecoxib are administered concurrently or sequentially, and wherein the plumbagin is present in a concentration in the range of 1 micromolar-100 micromolar and the celecoxib is present in a concentration in the range of 1 micromolar-100 micromolar.

Methods of treating cancer in a subject in need thereof are provided according to aspects of the present invention which include administering a pharmaceutical composition including a therapeutically effective amount of plumbagin and celecoxib to the subject, wherein the plumbagin is contained in liposomes without celecoxib, celecoxib is contained in liposomes without plumbagin or both celecoxib and plumbagin are separately contained in liposomes, wherein the plumbagin and/or celecoxib are administered concurrently or sequentially, and wherein the plumbagin is present in a concentration in the range of 0.1 micromolar-50 micromolar and the celecoxib is present in a concentration in the range of 2.5 micromolar-1250 micromolar.

Methods of treating cancer in a subject in need thereof are provided according to aspects of the present invention which include administering a pharmaceutical composition including liposomes containing plumbagin, liposomes containing celecoxib, or liposomes containing both plumbagin and celecoxib, wherein the liposomes include at least one polyethylene glycol modified neutral lipid, wherein the amount of polyethylene glycol modified neutral lipid is an amount in the range of 2.5-30 molar percent, inclusive, of total lipids in the liposomes; and one or more anionic, cationic or neutral lipids in an amount in the range of 70-97.5, inclusive, molar percent of total lipids in the liposomes.

Methods of treating cancer in a subject in need thereof are provided according to aspects of the present invention which include administering a pharmaceutical composition including liposomes containing plumbagin, liposomes containing celecoxib, or liposomes containing both plumbagin and celecoxib, wherein the liposomes include at least one polyethylene glycol modified neutral lipid, wherein the amount of polyethylene glycol modified neutral lipid is an amount in the range of 5-20 molar percent, inclusive, of total lipids in the liposomes; and one or more anionic, cationic or neutral lipids in an amount in the range of 80-95, inclusive, molar percent of total lipids in the liposomes.

Methods of treating cancer in a subject in need thereof are provided according to aspects of the present invention which include administering a pharmaceutical composition including liposomes containing plumbagin, liposomes containing celecoxib, or liposomes containing both plumbagin and celecoxib, wherein the liposomes include 1,2-dipalmitoyl-sn-glycero-3-phosphoethanolamine-N-[methoxy(polyethyl glycol)-200], wherein the amount of 1,2-dipalmitoyl-sn-glycero-3-phosphoethanolamine-N-[methoxy(polyethyl glycol)-200] is in the range of 2.5-30 molar percent, inclusive, of total lipids in the liposomes; and L-alpha-phosphatidylcholine in an amount in the range of 70-97.5, inclusive, molar percent of total lipids in the liposomes.

Methods of treating cancer in a subject in need thereof are provided according to aspects of the present invention which include administering a pharmaceutical composition including liposomes containing plumbagin, liposomes containing celecoxib, or liposomes containing both plumbagin and celecoxib, wherein the liposomes include 1,2-dipalmitoyl-sn-glycero-3-phosphoethanolamine-N-[methoxy(polyethyl glycol)-200], wherein the amount of 1,2-dipalmitoyl-sn-glycero-3-phosphoethanolamine-N-[methoxy(polyethyl glycol)-200] is in the range of 5-20 molar percent, inclusive, of total lipids in the liposomes; and L-alpha-phosphatidylcholine in an amount in the range of 80-95, inclusive, molar percent of total lipids in the liposomes.

Methods of treating cancer in a subject in need thereof are provided according to aspects of the present invention wherein the plumbagin and/or celecoxib are administered by a route selected from: intravenous, intramuscular, subcutaneous, intraperitoneal, oral, otic, rectal, vaginal, topical, parenteral, pulmonary, ocular, nasal, intratumoral and mucosal.

Methods of treating cancer in a subject in need thereof are provided according to aspects of the present invention wherein the plumbagin and/or celecoxib are administered by an intravenous route of administration.

Methods of treating cancer in a subject in need thereof are provided according to aspects of the present invention wherein the plumbagin and/or celecoxib are administered intratumorally.

Methods of treating cancer in a subject in need thereof are provided according to aspects of the present invention wherein the plumbagin and/or celecoxib are administered topically.

Methods of treating cancer in a subject in need thereof are provided according to aspects of the present invention wherein the subject is human.

Methods of treating cancer in a subject in need thereof are provided according to aspects of the present invention wherein the subject has skin cancer.

Methods of treating cancer in a subject in need thereof are provided according to aspects of the present invention wherein the subject has basal cell carcinoma, squamous cell carcinoma or malignant melanoma.

Methods of treating cancer in a subject in need thereof are provided according to aspects of the present invention wherein the cancer is cancer of the liver, prostate, breast, brain, stomach, pancreas, blood cells, uterus, cervix, ovary, lung, colon, or connective tissue.

Methods of treating cancer in a subject in need thereof are provided according to aspects of the present invention, wherein the cancer is characterized by abnormal activation of COX-2 and STAT3.

Methods of treating cancer in a subject in need thereof are provided according to aspects of the present invention which further include assay of COX-2 and/or STAT3 to detect abnormal activation of COX-2 and/or STAT3 in a sample obtained from the subject containing cancer cells.

Methods of treating cancer in a subject in need thereof are provided according to aspects of the present invention which further include administration of an adjunct anti-cancer treatment.

Commercial packages are provided according to aspects of the present invention which include: plumbagin; celecoxib; and instructions for use of plumbagin and celecoxib in treating cancer in a subject in need thereof.

Commercial packages are provided according to aspects of the present invention which include a pharmaceutical composition including: plumbagin, celecoxib and a pharmaceutically acceptable carrier; and instructions for use of plumbagin and celecoxib in treating cancer in a subject in need thereof.

Commercial packages are provided according to aspects of the present invention which include a pharmaceutical composition including: plumbagin and celecoxib contained together in liposomes; and instructions for use of plumbagin and celecoxib in treating cancer in a subject in need thereof.

Commercial packages are provided according to aspects of the present invention which include a pharmaceutical composition including: plumbagin contained in liposomes without celecoxib and celecoxib contained in liposomes without plumbagin; and instructions for use of plumbagin and celecoxib in treating cancer in a subject in need thereof.

DETAILED DESCRIPTION

Figure 1A:
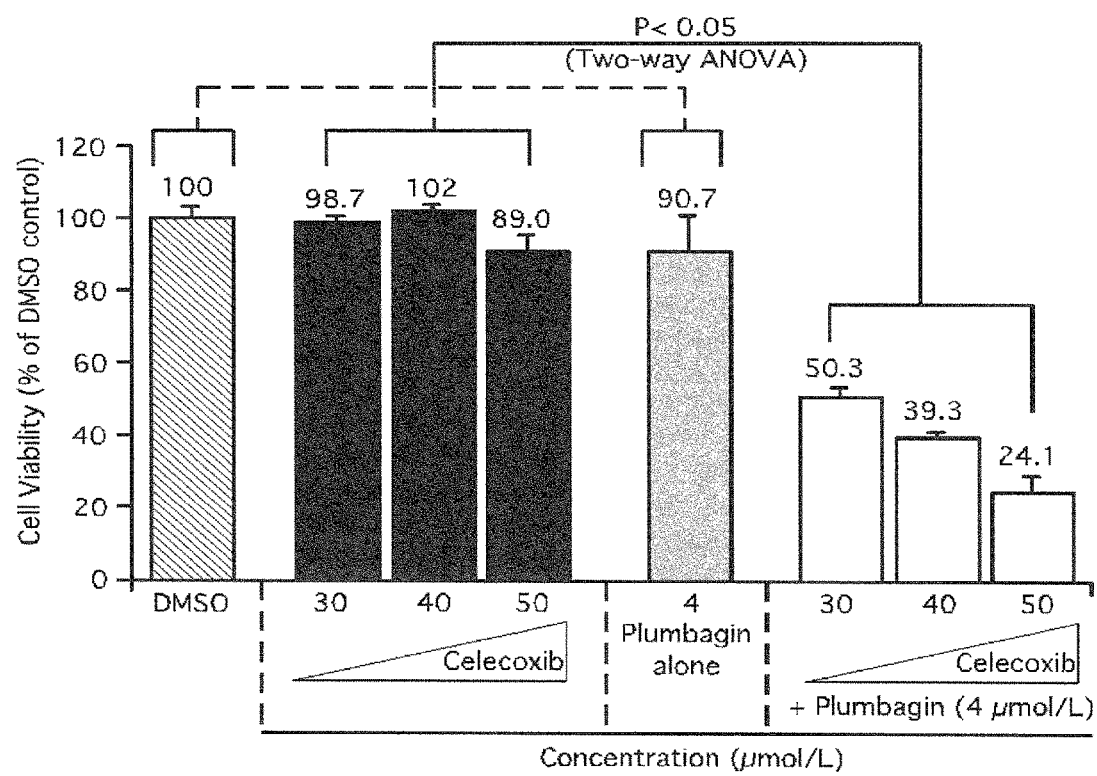
FIG. 1A is a graph showing results of treatment of UACC 903 melanoma cells with 30, 40 or 50 μmol/L of celecoxib, 4 μmol/L of plumbagin and combinations of 30, 40 or 50 μmol/L, of celecoxib, 4 μmol/L of plumbagin and resulting changes in cell viability as % of DMSO control.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Chu, E. and Devita, V. T., Eds., Physicians' Cancer Chemotherapy Drug Manual, Jones & Bartlett Publishers, 2005; J. M. Kirkwood et al., Eds., Current Cancer Therapeutics, 4th Ed., Current Medicine Group, 2001; Remington: The Science and Practice of Pharmacy, Lippincott Williams & Wilkins, 21st Ed., 2006; L. V. Allen, Jr. et al., Ansel's Pharmaceutical Dosage Forms and Drug Delivery Systems, 8th Ed., Philadelphia, Pa.: Lippincott, Williams & Wilkins, 2004; and L. Brunton et al., Goodman & Gilman's The Pharmacological Basis of Therapeutics, McGraw-Hill Professional, 11th Ed., 2005.

The singular terms "a," "an," and "the" are not intended to be limiting and include plural referents unless explicitly stated otherwise or the context clearly indicates otherwise.

Compositions and methods for treating cancer are provided according to the present invention.

Compositions according to aspects of the present invention prevent and inhibit cancer cell multiplication and tumor development and are considered useful as chemotherapeutic and chemopreventive agents. Methods including administration of celecoxib and plumbagin to a subject in need thereof are provided according to particular aspects of the present invention which have utility, for example, in inhibiting cancer cells.

Compositions and methods for treating cancer are provided according to the present invention which inhibit cyclins as well as the COX-2 and STAT3 pathways abnormally activated in melanoma and other cancers and thereby inhibit abnormal cell survival and proliferation. Cyclins are key to the functioning of the cyclin-cyclin dependent kinase complex in melanoma cells. Mechanisms leading to reduction in the proliferative potential of melanoma cells following treatment with celecoxib and plumbagin according to methods of the present invention appear to be mediated through reductions in the levels of key cyclins, cyclins A2, B1, D1 and H. Apoptosis appears to be mediated through decreased levels of active STAT3.

It is appreciated that compositions and methods according to aspects described herein are useful to inhibit cancer cells in vitro and in vivo.

Compositions and Pharmaceutical Compositions

In certain aspects, the present invention relates to compositions including celecoxib, compositions including plumbagin and compositions including both celecoxib and plumbagin.

Plumbagin (5-hydroxy-2-methyl-1,4-napthoquinone) is a quinoid isolated from the roots of the plant *Plumbago zeylanica*, see for example Hafeez et al., Mol Oncol. 2012 Dec. 14. pii: S1574-7891(12)00127-5. doi: 10.1016/j.molonc.2012.12.001; Hafeez et al., Int J Cancer. 2012; 131:2175-86; Li et al., Acta Pharmacol Sin. 2012; 33:242-9. Plumbagin can be obtained commercially, isolated from natural sources or chemically synthesized according to known methods.

Celecoxib, 4-[5-(4-Methylphenyl)-3-(trifluoromethyl)-1H-pyrazol-1-yl]benzenesulfonamide, is a drug that inhibits cyclooxygenase-2 (COX-2) activity. Celecoxib can be obtained commercially or chemically synthesized according to known methods.

In certain aspects, the present invention relates to liposomal compositions including celecoxib, liposomal compositions including plumbagin and liposomal compositions including both celecoxib and plumbagin.

Compositions and pharmaceutical compositions including celecoxib may be provided as a pharmaceutically acceptable salt, hydrate, amide or ester of celecoxib according to aspects of the present invention. Compositions including plumbagin may be provided as a pharmaceutically acceptable salt, hydrate, amide or ester of plumbagin according to aspects of the present invention.

Compositions and pharmaceutical compositions according to the present invention encompass stereoisomers of celecoxib and plumbagin. Compositions according to the present invention encompass the individual enantiomers of celecoxib and plumbagin, as well as wholly or partially racemic mixtures of any of these.

Pharmaceutical compositions including celecoxib, plumbagin and a pharmaceutically acceptable carrier in particular aspects of the present invention.

The term "pharmaceutically acceptable carrier" refers to a carrier which is substantially non-toxic to a subject to which the composition is administered and which is substantially chemically inert with respect to the active component or components.

A pharmaceutical composition according to the invention generally includes about 0.1-99% of celecoxib, plumbagin or both celecoxib and plumbagin.

Advantageously, anti-cancer compounds according to aspects of the present invention are formulated to achieve lipid-solubility and/or aqueous-solubility.

In particular aspects, a pharmaceutically acceptable carrier is a particulate carrier such as lipid particles including liposomes, micelles, unilamellar or mulitlamellar vesicles; polymer particles such as hydrogel particles, polyglycolic acid particles or polylactic acid particles; inorganic particles such as calcium phosphate particles such as described in for example U.S. Pat. No. 5,648,097; and inorganic/organic particulate carriers such as described for example in U.S. Pat. No. 6,630,486.

A particulate pharmaceutically acceptable carrier can be selected from among a lipid particle, particularly liposomes; a polymer particle; an inorganic particle; and an inorganic/organic particle. A mixture of particle types can also be included as a particulate pharmaceutically acceptable carrier.

A particulate carrier is typically formulated such that particles have an average particle size in the range of about 1 nm-10 microns. In particular aspects, a particulate carrier is formulated such that particles have an average particle size in the range of about 1 nm-500 nm, particularly, 20 nm-250 nm and more particularly 50 nm-150 nm.

Aspects of pharmaceutical compositions of the present invention include a lipid-based carrier. The term "lipid-based carrier" refers to macromolecular structures having lipid and/or lipid derivatives as the major constituent.

Lipids included in lipid-based carriers can be naturally-occurring lipids, synthetic lipids or combinations thereof.

A lipid-based carrier is formulated as a liposome for use in compositions, kits and methods according to aspects of the invention. The term "liposome" refers to a bilayer particle of amphipathic lipid molecules enclosing an aqueous interior space. Liposomes are typically produced as small unilammellar vesicles (SUVs), large unilammellar vesicles (LUVs) or multilammellar vesicles (MLVs). Celecoxib and plumbagin are associated with liposomes by encapsulation in the aqueous interior space of the liposomes, disposed in the lipid bilayer of the liposomes and/or associated with the liposomes by binding, such as ionic binding or association by van der Waals forces. Thus, celecoxib and/or plumbagin is contained in liposomes when it is encapsulated in the aqueous interior space of the liposomes, disposed in the lipid bilayer of the liposomes and/or associated with the liposomes by binding, such as ionic binding or association by van der Waals forces. Liposomes according to aspects of the invention are generally in the range of about 1 nanometer-1 micron in diameter although they are not limited with regard to size.

A pharmaceutical composition includes a liposomal formulation of celecoxib in particular aspects of the present invention.

A pharmaceutical composition includes a liposomal formulation of plumbagin in particular aspects of the present invention.

A pharmaceutical composition includes a liposomal formulation of celecoxib and plumbagin in combination in particular aspects of the present invention.

Liposomal formulations of celecoxib and/or plumbagin according to aspects of the present invention include can include one or more types of neutral, cationic lipid and/or anionic lipid, such that the liposomal formulations have a net neutral surface charge at physiological pH. According to aspects, a PEG-modified lipid is included.

The term cationic lipid refers to any lipid which has a net positive charge at physiological pH. Examples of cationic lipids include, but are not limited to, N-(1-(2,3-dioleyloxy)propyl)-N,N,N-trimethylammonium chloride (DOTMA); 1,2-dioleoyloxy-3-(trimethylammonium)propane (DOTAP); 1,2-dioleoyl-3-dimethyl ammonium-propane (DODAP); dioctadecylamidoglycylspermine (DOGS); 1,2-dipalmitoylphosphatidylethanolamidospermine (DPPES); 2,3-dioleyloxy-N-(2-(sperminecarboxamido)ethyl)-N,N-dimethyl-1-propanaminium trifluoroacetate (DOSPA); dimyristoyltrimethylammonium propane (DMTAP); (3-dimyristyloxypropyl)(dimethyl)(hydroxyethyl)ammonium (DMRIE); dioctadecyldimethylammonium chloride (DODAC), Dimethyldidodecylammonium bromide (DDAB); 3β[N—(N',N'-dimethylaminoethane)-carbamoyl] cholesterol (DC-Chol); 1-[2-(9(Z)-octadecenoyloxy)-ethyl]-2-(8(Z)-heptadecenyl)-3-(2-hydroxyethyl)-imidazolinium (DOTIM); bis-guanidinium-spermidine-cholesterol (BGTC); bis-guanidinium-tren-cholesterol (BGTC); 1,3-Dioleoyloxy-2-(6-carboxy-spermyl)-propylamid (DOSPER) N-[3-[2-(1,3-dioleoyloxy)propoxy-carbonyl]propyl]-N,N,N-trimethylammonium iodide (YKS-220); as well as pharmaceutically acceptable salts and mixtures thereof. Additional examples of cationic lipids are described in Lasic and Papahadjopoulos, Medical Applications of Liposomes, Elsevier, 1998; U.S. Pat. Nos. 4,897,355; 5,208,036; 5,264,618; 5,279,833; 5,283,185; 5,334,761; 5,459,127; 5,736,392; 5,753,613; 5,785,992; 6,376,248; 6,586,410; 6,733,777; and 7,145,039.

The term neutral lipid refers to any lipid which has no net charge, either uncharged or in neutral charge zwitterionic form, at physiological pH. Examples of neutral lipids include, but are not limited to, L-alpha-phosphatidylcholine (ePC), distearoylphosphatidylcholine (DSPC), dioleoyl-phosphatidylethanolamine (DOPE), distearoylphosphatidylethanolamine (DSPE); 1,2-dioleoyl-sn-glycero-3-Phosphocholine (DOPC), 1,2-dipalmitoyl-sn-glycero-3-phosphoethanolamine (DPPE), cephalin, ceramide, cerebrosides, cholesterol, diacylglycerols, and sphingomyelin.

The term anionic lipid refers to any lipid which has a net negative charge at physiological pH. Examples of anionic lipids include, but are not limited to, dihexadecylphosphate (DhP), phosphatidyl inositols, phosphatidyl serines, such as dimyristoyl phosphatidyl serine, and dipalmitoyl phosphatidyl serine, phosphatidyl glycerols, such as dimyristoyl-phosphatidyl glycerol, dioleoylphosphatidyl glycerol, dilauryloylphosphatidyl glycerol, dipalmitoylphosphatidyl glycerol, distearyloylphosphatidyl glycerol, phosphatidic acids, such as dimyristoyl phosphatic acid and dipalmitoyl phosphatic acid and diphosphatidyl glycerol.

The term "modified lipid" refers to lipids modified to aid in, for example, inhibiting aggregation and/or precipitation, inhibiting immune response and/or improving half-life in circulation in vivo. Modified lipids include, but are not limited to, pegylated lipids, such as polyethyleneglycol 2000 distearoylphosphatidylethanolamine (PEG(2000) DSPE); 1,2-dipalmitoyl-sn-glycero-3-phosphoethanolamine-N-[methoxy(polyethylene glycol)-2000] (DPPE-PEG-2000), and polyethyleneglycol 750 octadecylsphingosine (PEG (750) C8).

Exemplary ratios of lipid components included in liposomal formulations of the present invention are neutral lipid:polyethyleneglycol modified neutral lipid—80:20 mol %.

For example, liposomal formulations of celecoxib, plumbagin or both celecoxib and plumbagin include L-alpha-phosphatidylcholine and 1,2-dipalmitoyl-sn-glycero-3-phosphoethanolamine-N-[methoxy(polyethylene glycol)-2000] in an 80:20 mol % ratio according to aspects of the present invention.

According to aspects of the present invention, liposomal formulations of celecoxib, plumbagin or both celecoxib and plumbagin include at least one polyethylene glycol modified neutral lipid, wherein the total amount of polyethylene glycol modified neutral lipid is an amount in the range of 10-30 molar percent, inclusive, such as 15-25 molar percent polyethylene glycol modified neutral lipid and further including one or more anionic, cationic or neutral lipids.

According to aspects of the present invention, liposomal formulations of celecoxib, plumbagin or both celecoxib and plumbagin include at least one polyethylene glycol modified neutral lipid, wherein the total amount of polyethylene glycol modified neutral lipid is an amount in the range of 10-30 molar percent, inclusive, such as 15-25 molar percent polyethylene glycol modified neutral lipid and further including one or more anionic, cationic or neutral lipids, with the proviso that the resulting liposomes have a net neutral surface charge at physiological pH.

In addition to containing of celecoxib, plumbagin or both celecoxib and plumbagin, liposomes of the present invention optionally contain any of a variety of useful biologically active molecules and substances including, but not limited to, adjunct therapeutics, proteins, peptides, carbohydrates, oligosaccharides, drugs, and nucleic acids capable of being complexed with the liposomes. The term "biologically active molecules and substances" refers molecules or substances that exert a biological effect in vitro and/or in vivo, such as, but not limited to, nucleic acids, inhibitory RNA, siRNA, shRNA, ribozymes, antisense nucleic acids, antibodies, hormones, small molecules, aptamers, decoy molecules and toxins.

Liposomes are generated using well-known standard methods, including, but not limited to, solvent/hydration methods, ethanol or ether injection methods, freeze/thaw methods, sonication methods, reverse-phase evaporation methods, and surfactant methods. Liposomes and methods relating to their preparation and use are found in Liposomes: A Practical Approach (The Practical Approach Series, 264), V. P. Torchilin and V. Weissig (Eds.), Oxford University Press; 2nd ed., 2003; N. Duzgunes, Liposomes, Part A, Volume 367 (Methods in Enzymology) Academic Press; 1st ed., 2003; L. V. Allen, Jr. et al., Ansel's Pharmaceutical Dosage Forms and Drug Delivery Systems, 8th Ed., Philadelphia, Pa.: Lippincott, Williams & Wilkins, 2005, pp. 663-666; and A. R. Gennaro, Remington: The Science and Practice of Pharmacy, Lippincott Williams & Wilkins, 21st ed., 2005, pp. 766-767.

In particular aspects, compositions of the present invention are formulated for topical application. In further particular aspects, compositions of the present invention are formulated for topical application and are characterized by less than 10% absorption of an active ingredient in the composition into the system of an individual treated topically. In still further particular aspects, compositions of the present invention are formulated for topical application and are characterized by less than 9%, 8%, 7%, 6%, 5%, 4%, 3%, 2%, 1% absorption of an active ingredient in the composition into the system of an individual treated topically. Absorption into the system of an individual can be measured by any of various methods, particularly assay for the active ingredient, a metabolite and/or a breakdown product of the active ingredient in a sample obtained from an individual treated with the topical formulation. For example, a blood, plasma or serum sample can be assayed for presence of the active ingredient, a metabolite of the active ingredient and/or a breakdown product of the active ingredient.

Pharmaceutical compositions provided according to aspects of the present invention are suitable for administration to a subject by a variety of systemic and/or local routes including, but not limited to, intravenous, intramuscular, subcutaneous, intraperitoneal, oral, otic, rectal, vaginal, topical, parenteral, pulmonary, ocular, nasal, intratumoral and mucosal.

A topical formulation can be an ointment, lotion, cream or gel in particular aspects. Topical dosage forms such as ointment, lotion, cream or gel bases are described in Remington: The Science and Practice of Pharmacy, $21^{st}$ Ed., Lippincott Williams & Wilkins, 2006, p. 880-882 and p. 886-888; and in Allen, L. V. et al., Ansel's Pharmaceutical Dosage Forms and Drug Delivery Systems, $8^{th}$ Ed., Lippincott Williams & Wilkins, 2005, p. 277-297.

Pharmaceutical compositions suitable for delivery to a subject may be prepared in various forms illustratively including physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate. Additional components illustratively including a buffer, a solvent, or a diluent may be included.

Such formulations are administered by a suitable route including parenteral and oral administration. Administration may include systemic or local injection, and particularly intravenous injection.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature. Prolonged delivery of an injectable pharmaceutical form can be brought about by the use of agents delaying absorption, for example, aluminum monostearate and gelatin.

Solid dosage forms for oral administration include capsules, tablets, pills, powders, and granules. In such solid dosage forms, one or more anti-cancer compounds described herein is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, plant starches such as potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, glycerol monostearate, and glycols (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also include a buffering agent.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include a pharmaceutically acceptable carrier formulated as an emulsion, solution, suspension, syrup, or elixir. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to celecoxib and/or plumbagin, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and the like.

Pharmaceutically acceptable carriers and formulation of pharmaceutical compositions are known in the art, illustratively including, but not limited to, as described in Remington: The Science and Practice of Pharmacy, 21$^{st}$ Ed., Lippincott, Williams & Wilkins, Philadelphia, Pa., 2006; and Allen, L. V. et al., Ansel's Pharmaceutical Dosage Forms and Drug Delivery Systems, 8$^{th}$ Ed., Lippincott, Williams & Wilkins, Philadelphia, Pa., 2005.

A "pharmaceutically acceptable" salt, ester, amide or solvate is suitable for use in a subject without undue toxicity or irritation to the subject and is effective for their intended use.

Pharmaceutically acceptable salts include pharmaceutically acceptable acid addition salts and base addition salts.

Pharmaceutically acceptable salts are well-known in the art, such as those detailed in S. M. Berge et al., J. Pharm. Sci., 66:1-19, 1977. Exemplary pharmaceutically acceptable salts are those suitable for use in a subject without undue toxicity or irritation to the subject and which are effective for their intended use which are formed with inorganic acids such as hydrochloric acid, hydrobromic acid, hydroiodic acid, nitric acid, phosphoric acid, sulfuric acid and sulfamic acid; organic acids such as acetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, formic acid, fumaric acid, glutamic acid, glycolic acid, glycerophosphoric acid, hemisulfic acid, heptanoic acid, hexanoic acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, trichloroacetic acid, trifluoroacetic acid and undecanoic acid; inorganic bases such as ammonia, hydroxide, carbonate, and bicarbonate of ammonium; organic bases such as primary, secondary, tertiary and quaternary amine compounds ammonium, arginine, betaine, choline, caffeine, diolamine, diethylamine, diethanolamine, 2-dimethylaminoethanol, 2-diethylaminoethanol, dicyclohexylamine, dicyclohexylamine, dibenzylamine, N, N-dibenzylphenethylamine, 1-ephenamine, N, N'-dibenzylethylenediamine, ethanolamine, ethylamine, ethylenediamine, glucosamine, histidine, hydrabamine, isopropylamine, 1 h-imidazole, lysine, methylamine, N-ethylpiperidine, N-methylpiperidine, N-methylmorpholine, N, N-dimethylaniline, piperazine, trolamine, methylglucamine, purines, piperidine, pyridine, theobromine, tetramethylammonium compounds, tetraethylammonium compounds, trimethylamine, triethylamine, tripropylamine and tributylamine and metal cations such as aluminum, calcium, copper, iron, lithium, magnesium, manganese, potassium, sodium, and zinc.

Pharmaceutically acceptable solvates illustratively include hydrates, ethanolates, methanolates.

Exemplary pharmaceutically acceptable amides include amides derived from ammonia, primary C1-C6 alkyl amines and secondary C1-C6 dialkyl amines including those in the form of a 5- or 6-member nitrogen-containing heterocycle.

Compositions including celecoxib and plumbagin according to aspects of the present invention have various utilities such as, but not limited to, utility in treatment of a subject having cancer or at risk of having cancer, such as skin cancer and other cancers including, but not limited to, cancers of the liver, prostate, breast, brain, stomach, pancreas, blood cells, uterus, cervix, ovary, lung, colon, connective tissues (sarcomas) and other soft tissues.

Compositions including celecoxib and plumbagin according to aspects of the present invention have utility in treatment of a subject having skin cancer or at risk of having skin cancer, including basal cell carcinoma, squamous cell carcinoma and malignant melanoma.

Methods of Treatment

Methods for treatment and/or prevention of pathological conditions in a subject are provided including administration of celecoxib and plumbagin according to aspects of the present invention.

Methods for treatment and/or prevention of pathological conditions in a subject are provided including administration of both celecoxib and plumbagin show synergistic effects.

Methods for treatment and/or prevention of pathological conditions in a subject are provided including administration of both celecoxib and plumbagin allow for reduced effective dosage and increased therapeutic index of celecoxib and/or plumbagin.

According to aspects, combination therapies include: (1) administration of pharmaceutical compositions of the present invention that include celecoxib and plumbagin in combination; (2) co-administration of celecoxib and plumbagin wherein the celecoxib and plumbagin are not formulated in the same composition. When using separate formulations, celecoxib and plumbagin may be administered at the same time, or celecoxib may be administered at intermittent times, staggered times, prior to, subsequent to, or combinations thereof, with reference to the administration of plumbagin.

Methods for treatment and/or prevention of pathological conditions in a subject are provided including administration of liposomal compositions including celecoxib, liposomal compositions including plumbagin or liposomal compositions including both celecoxib and plumbagin according to aspects of the present invention.

Particular cancers treated using methods and compositions described herein are characterized by abnormal cell proliferation including, but not limited to, pre-neoplastic hyperproliferation, cancer in-situ, neoplasms and metastasis. Methods and compositions of the present invention can be used for prophylaxis as well as amelioration of signs and/or symptoms of cancer. The terms "treating" and "treatment" used to refer to treatment of a cancer in a subject include: preventing, inhibiting or ameliorating the cancer in the subject, such as slowing progression of the cancer and/or reducing or ameliorating a sign or symptom of the cancer.

A therapeutically effective amount of celecoxib and plumbagin administered according to aspects of the present invention is an amount which has a beneficial effect in a subject being treated. In subjects having cancer or at risk for having cancer, such as a condition characterized by abnormal cell proliferation including, but not limited to, pre-neoplastic hyperproliferation, cancer in-situ, neoplasms, metastasis, a tumor, a benign growth or other condition responsive to an inventive composition, a therapeutically effective amount of a composition is effective to ameliorate or prevent one or more signs and/or symptoms of the condition. For example, a therapeutically effective amount of a composition including celecoxib and plumbagin is effective to detectably increase apoptosis and/or decrease proliferation of cells of a cancer condition characterized by abnormal cell proliferation including, but not limited to, pre-neoplastic hyperproliferation, cancer in-situ, neoplasms, metastasis, a tumor, a benign growth or other condition responsive to an inventive composition.

Methods of treating a subject are provided according to aspects of the present invention which include administering a therapeutically effective amount of celecoxib and plumbagin to a subject in need thereof, wherein the subject has an abnormal proliferative condition, such as cancer, pre-neoplastic hyperproliferation, cancer in-situ, neoplasms, metastasis, tumor or benign growth.

Subjects are identified as having, or at risk of having, cancer using well-known medical and diagnostic techniques.

The term "subject" refers to an individual in need of treatment for a pathological condition responsive to the beneficial effects of compositions of the present invention, particularly cancer. While the present invention describes compositions and methods for treatment of human subjects in need thereof, the present invention is not limited to human subjects and the term subject generally includes mammals and birds, such as, but not limited to, non-human primates, cats, dogs, cows, horses, rodents, pigs, sheep, goats and poultry.

Methods of treatment according to aspects of the present invention include administration of celecoxib and plumbagin to a subject having skin cancer or at risk of having skin cancer, including basal cell carcinoma, squamous cell carcinoma and malignant melanoma.

Methods of treatment according to aspects of the present invention include administration of celecoxib and plumbagin to a subject having cancer or at risk of having cancer, such as, but not limited to, cancers of the liver, prostate, breast, brain, stomach, pancreas, blood cells, uterus, cervix, ovary, lung, colon, connective tissues (sarcomas) and other soft tissues.

Methods of treatment of a subject having, or at risk of having, cancer, are provided according to aspects of the present invention including administration of a pharmaceutically effective amount of liposomes containing including celecoxib, liposomes containing plumbagin or liposomes containing both celecoxib and plumbagin.

Liposomal formulations of anti-cancer compositions of the present invention are injected intravenously and/or applied topically according to aspects of the present invention.

Celecoxib and plumbagin are administered to a subject by any of a variety of systemic and/or local routes according to aspects of methods of the present invention including, but not limited to, intravenous, intramuscular, subcutaneous, intraperitoneal, oral, otic, rectal, vaginal, topical, parenteral, pulmonary, ocular, nasal, intratumoral and mucosal.

Celecoxib and plumbagin may be administered acutely or chronically according to aspects of methods of the present invention.

Celecoxib and plumbagin may be administered: together in a single formulation; both separately; together or both separately as a unitary dose; or together or both separately in multiple doses. Celecoxib and plumbagin may be administered together in a single formulation; both separately; together or both separately as a unitary dose; or together or both separately in multiple doses over a relatively limited period of time, such as seconds-hours. In a further embodiment, administration may include multiple doses of celecoxib and plumbagin administered together in a single formulation, or separately, administered over a period of days-years, such as for chronic treatment of cancer.

A therapeutically effective amount of celecoxib and plumbagin according to the present invention will vary depending on the particular pharmaceutical composition used, the severity of the condition to be treated, the species of the subject, the age and sex of the subject and the general physical characteristics of the subject to be treated. One of skill in the art could determine a therapeutically effective amount in view of these and other considerations typical in medical practice. In general it is contemplated that a therapeutically effective amount would be in the range of about 0.001 mg/kg-100 mg/kg body weight, optionally in the range of about 0.01-10 mg/kg, and further optionally in the range of about 0.1-5 mg/kg. Further, dosage may be adjusted depending on whether treatment is to be acute or continuing.

Combination Treatments

Combinations of therapeutic agents are administered according to aspects of the present invention. In some aspects, celecoxib, plumbagin and at least one additional therapeutic agent are administered to a subject to treat cancer in a subject in need thereof. In still further aspects, celecoxib, plumbagin and at least two additional therapeutic agents are administered to a subject to treat cancer in a subject in need thereof.

The term "additional therapeutic agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents included in aspects of methods and compositions of the present invention include, but are not limited to, antibiotics, antivirals, antineoplastic agents, analgesics, antipyretics, antidepressants, antipsychotics, anti-cancer agents, antihistamines, anti-osteoporosis agents, anti-osteonecrosis agents, antiinflammatory agents, anxiolytics, chemotherapeutic agents, diuretics, growth factors, hormones, non-steroidal anti-inflammatory agents, steroids and vasoactive agents.

Treatments including administration of both celecoxib and plumbagin show synergistic effects. Combination therapies utilizing celecoxib, plumbagin and one or more additional therapeutic agents may show further synergistic effects.

According to aspects of the present invention, combination therapies include: (1) administration of pharmaceutical compositions that include celecoxib and plumbagin of the present invention in combination with one or more additional therapeutic agents; (2) co-administration of celecoxib and plumbagin with one or more additional therapeutic agents wherein none of celecoxib, plumbagin and the one or more additional therapeutic agents are formulated in the same composition and (3) co-administration of celecoxib and plumbagin with one or more additional therapeutic agents wherein celecoxib and plumbagin are formulated in the same composition and wherein the one or more additional therapeutic agents have not been formulated in the same composition. When using separate formulations, celecoxib, plumbagin and the one or more additional therapeutic agents may be administered at the same time or at different times; and two or more of celecoxib, plumbagin and the one or more additional therapeutic agents may be administered at the same time or at different times with reference to the other therapeutic agents.

Combination treatments including celecoxib and plumbagin with one or more additional therapeutic agents can allow for reduced effective dosage and increased therapeutic index of the compositions of the present invention and the one or more additional therapeutic agents used in methods of the present invention.

Optionally, a method of treating a subject having cancer or at risk of having cancer further includes an adjunct anti-cancer treatment. An adjunct anti-cancer treatment can be administration of an anti-cancer agent.

Anti-cancer agents are described, for example, in Goodman et al., Goodman and Gilman's The Pharmacological Basis of Therapeutics, 8th Ed., Macmillan Publishing Co., 1990.

Anti-cancer agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflornithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochloride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

An adjunct anti-cancer treatment can be a radiation treatment of a subject or an affected area of a subject's body.

In particular aspects, cancers treated in a subject using methods and compositions described herein are characterized by abnormal activation of COX-2 and STAT3.

Increased levels or activity of one or both of COX-2 and STAT3 is determined, for instance, by measurement of gene copy number, protein or RNA levels in cells known or suspected to be dysplasic, pre-cancerous, cancerous, metastatic or otherwise characterized by abnormal cell proliferation compared to normal cells. Assays for abnormal activation of COX-2 and/or STAT3 include, but are not limited to phosphorylation assays, immunoassays and nucleic acid assays.

Commercial Packages

Commercial packages are provided according to aspects of the present invention for treating cancer in a subject in need thereof, including celecoxib and plumbagin; or a salt, stereoisomer, hydrate, amide or ester of celecoxib and/or plumbagin. One or more auxiliary components are optionally included in commercial packages of the present invention, such as a pharmaceutically acceptable carrier exemplified by a buffer, diluent or a reconstituting agent. Instructions for use of celecoxib and plumbagin in treating cancer in a subject in need thereof are optionally included in a commercial package according to aspects of the present invention.

A commercial package including a liposomal formulation of celecoxib or a salt, stereoisomer, hydrate, amide or ester thereof, plumbagin or a salt, stereoisomer, hydrate, amide or ester thereof or celecoxib and plumbagin, or a salt, stereoisomer, hydrate, amide or ester thereof; or a salt, stereoisomer, hydrate, amide or ester of either or both thereof.

Embodiments of inventive compositions and methods are illustrated in the following examples. These examples are provided for illustrative purposes and are not considered limitations on the scope of inventive compositions and methods.

EXAMPLES

Cell Lines and Culture Conditions

Human fibroblast FF2441 cells metastatic melanoma cell lines UACC 903 and 1205 Lu were maintained in DMEM (Invitrogen), supplemented with 10% FBS (Hyclone). Cell lines were maintained in a 37° C. humidified 5% $CO_2$ atmosphere incubator and periodically monitored for phenotypic and genotypic characteristics, and for tumorigenic potential.

Figure 2A:
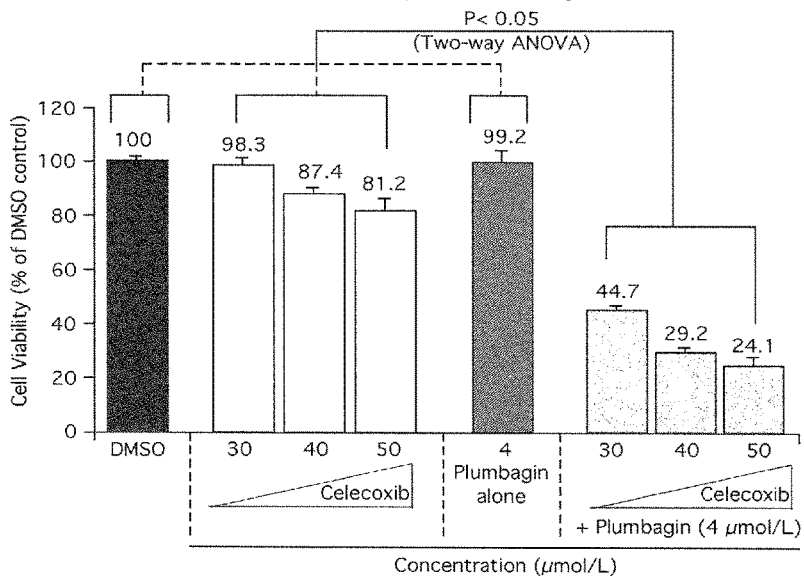
FIG. 2A is a graph showing results of treatment of 1205 Lu melanoma cells with 30, 40 or 50 μmol/L of celecoxib, 4 μmol/L of plumbagin and combinations of 30, 40 or 50 μmol/L of celecoxib, 4 μmol/L of plumbagin and resulting changes in cell viability as % of DMSO control.

Synergy Analysis when Treating Cultured Cells with Celecoxib and Plumbagin Dissolved in DMSO To identify agents that synergize with plumbagin a screen was undertaken identifying celecoxib as a possible agent that could cooperatively inhibit UACC 903 melanoma cell survival. To validate the initial screening result, plumbagin was maintained at 4 μmol/L and celecoxib was titrated at doses of 30, 40, and 50 μmol/L. UACC 903 and 1205 Lu melanoma cells were seeded into a 96-well plate at a density of $5 \times 10^3$ cells per well in 100 μL of media and grown for 48 h. Cells were then treated with 30, 40 or 50 μmol/L, of celecoxib (Sigma Chemical Co. St. Louis, Mo.) or 4 μmol/L of plumbagin (Sigma Chemical Co. St. Louis, Mo.) singly or in combination for 48-96 hours. Viability of the treated and control cells was measured by MTS assay (Promega, Madison, Wis.). $IC_{50}$ values for each compound in μmol/L for respective cell lines were measured from three independent experiments using GraphPad Prism version 4.01 (GraphPad Software, La Jolla, Calif.). Potential synergy between the drugs was assessed using the Chou-Talalay method to estimate the combination index (CI) using Calcusyn software, see T-C Chou and P. Talalay, Trends Pharmacol. Sci. 4, 450-454, 1983 and Chou T C, Talalay P., Adv Enzyme Regul 1984; 22: 27-55. Using this approach, combination index (CI) values <0.9 are synergistic, >1.1 is antagonistic, and values 0.9 to 1.1 are additive, see T-C Chou and P. Talalay, Trends Pharmacol. Sci. 4, 450-454, 1983 and Chou T C, Talalay P., Adv Enzyme Regul 1984; 22: 27-55. Results show that combining plumbagin with celecoxib leads to synergistic killing of melanoma cells. Simultaneous treatment with plumbagin and celecoxib significantly decreased the growth of UACC 903 and 1205 Lu cells compared with either plumbagin or celecoxib alone, celecoxib at 30 and pumbagin at 4 μmol/L versus both combined, celecoxib at 40 and plumbagin at 4 μmol/L versus both combined, and celecoxib at 50 and pumbagin at 4 μmol/L, versus both combined, as shown in FIGS. 1A & 2A; P<0.05, one-way ANOVA). FIG. 1A is a graph showing results of treatment of UACC 903 melanoma cells with 30, 40 or 50 μmol/L of celecoxib, 4 μmol/L of plumbagin and combinations of 30, 40 or 50 μmol/L of celecoxib, 4 μmol/L of plumbagin and resulting changes in cell viability as % of DMSO control.

Figure 1B:
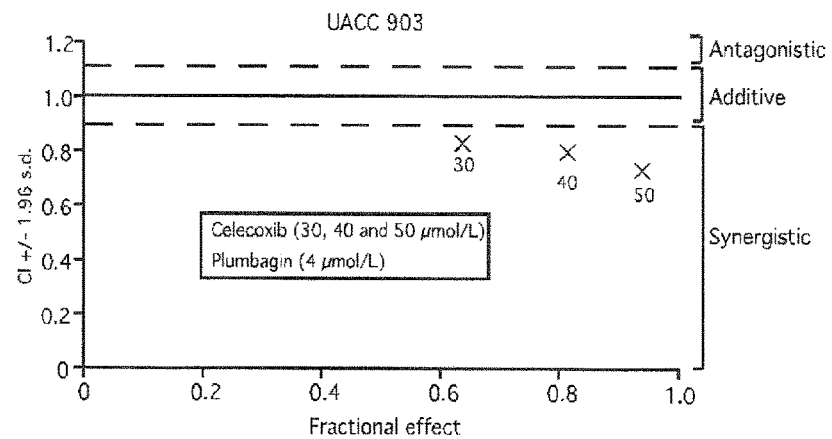
FIG. 1B is a graph showing that the estimated combination index (CI) values were in the range of 0.74 to 0.83, for 30, 40, and 50 μmol/L of celecoxib plus 4 μmol/L of plumbagin, respectively, in UACC 903 melanoma cells, indicating synergistically acting cooperative inhibition.
Figure 2B:
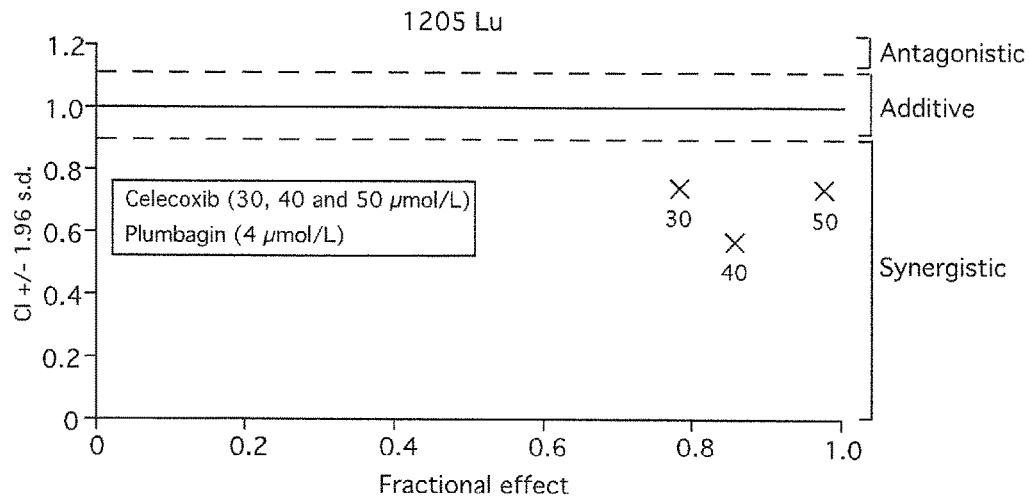
FIG. 2B is a graph showing that the estimated combination index (CI) values were in the range of 0.58-0.80 for 30, 40, and 50 μmol/L of celecoxib plus 4 μmol/L of plumbagin, respectively, in 1205 Lu melanoma cells, indicating synergistically acting cooperative inhibition.

FIG. 2A is a graph showing results of treatment of 1205 Lu melanoma cells with 30, 40 or 50 μmol/L of celecoxib, 4 μmol/L of plumbagin and combinations of 30, 40 or 50 μmol/L of celecoxib, 4 μmol/L of plumbagin and resulting changes in cell viability as % of DMSO control. FIG. 1B is a graph showing that the estimated combination index (CI) values were in the range of 0.74 to 0.83, for 30, 40, and 50 μmol/L of celecoxib plus 4 μmol/L of plumbagin, respectively, in UACC 903 melanoma cells, indicating synergistically acting cooperative inhibition. FIG. 2B is a graph showing that the estimated combination index (CI) values were in the range of 0.58-0.80 for 30, 40, and 50 μmol/L of celecoxib plus 4 μmol/L of plumbagin, respectively, in 1205 Lu melanoma cells, indicating synergistically acting cooperative inhibition. Thus, treatment of cultured melanoma cells with plumbagin and celecoxib of ratios of 1:7.5, 1:10 or 1:12.5 lead to cooperatively synergistic inhibition. Based on this observation ratios of 1:10 and 1:20 were selected for subsequent studies.

Figure 3:
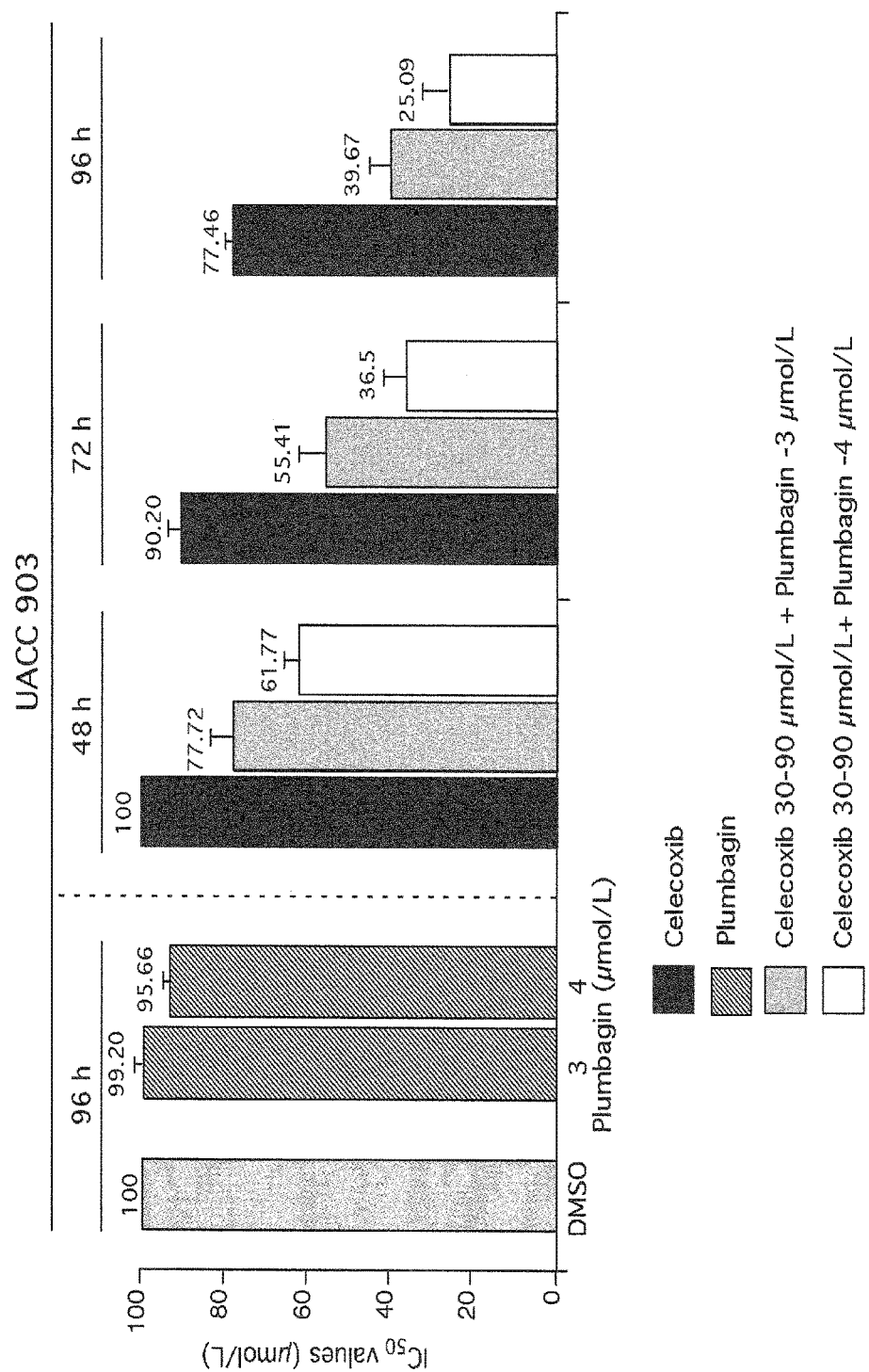
FIG. 3 is a graph showing effects of combinations of celecoxib and plumbagin to synergistically inhibit UACC 903 melanoma cells.
Figure 4:
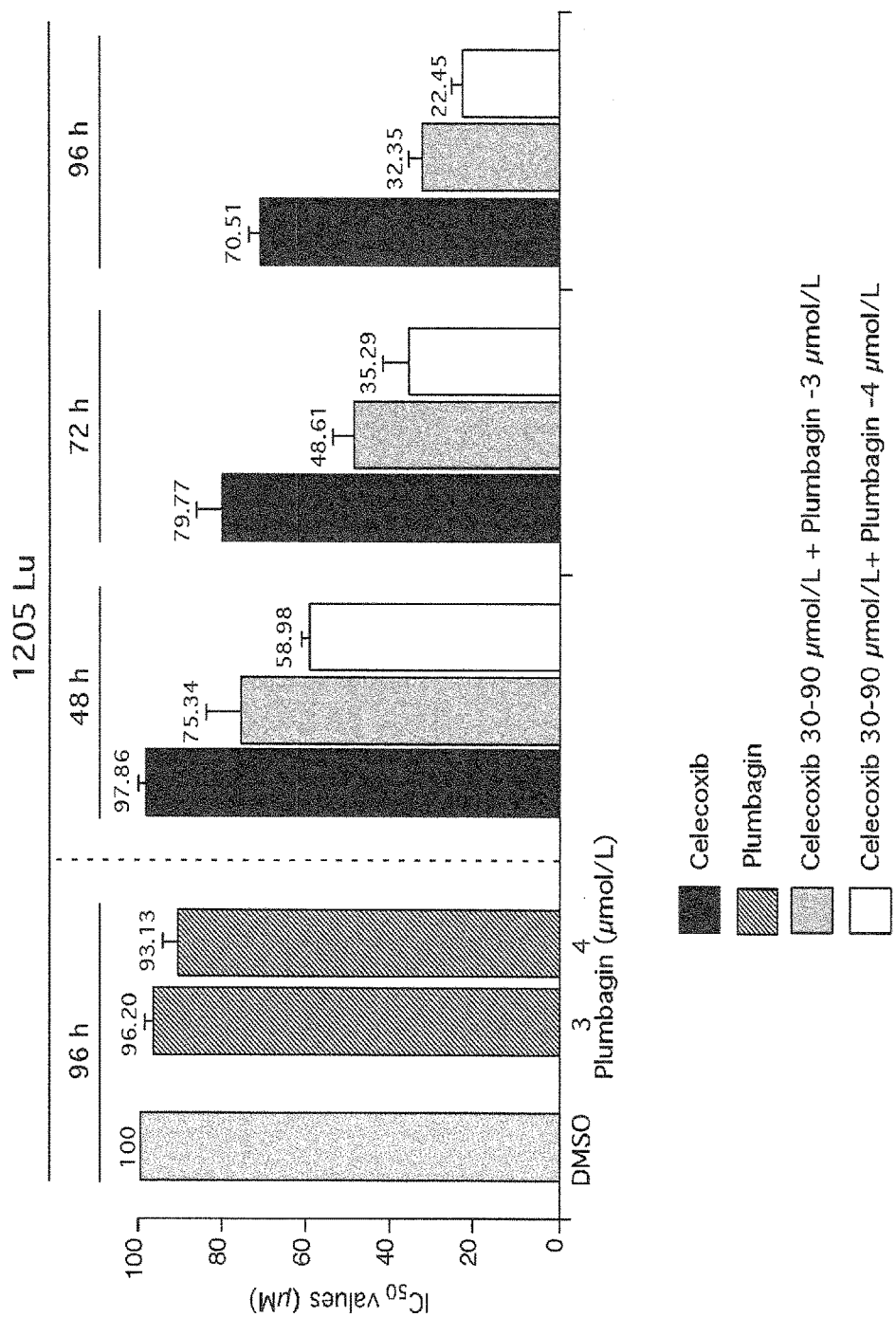
FIG. 4 is a graph showing effects of combinations of celecoxib and plumbagin to synergistically inhibit 1205 Lu melanoma cells.

Melanoma cell killing efficacy of agents alone and in combination treatment of melanoma cell lines UACC 903 and 1205 Lu. Plumbagin was used at 4 μmol/L and celecoxib was titrated at doses of 30-90 μmol/L to treat UACC 903 and 1205 Lu melanoma cells. Simultaneous treatment with plumbagin and celecoxib significantly decreased the growth of UACC 903 and 1205 Lu melanoma cells compared with either plumbagin or celecoxib alone. Average $IC_{50}$ of celecoxib ranged from 70-77 μmol/L at 96 hours of treatment compared to DMSO treated cells. Furthermore, in combination with plumbagin 4 μmol/L decreased significantly in $IC_{50}$ values ranged from 22-25 mol/L, as shown in FIGS. 3 & 4. FIG. 3 is a graph showing effects of combinations of celecoxib and plumbagin to synergistically inhibit UACC 903 melanoma cells. FIG. 4 is a graph showing effects of combinations of celecoxib and plumbagin to synergistically inhibit 1205 Lu melanoma cells.

Tumorigenicity Assessments—Non-Liposomal Celecoxib, Non-Liposomal Plumbagin

Tumor kinetics were measured by subcutaneous (s.c.) injection of $1 \times 10^6$ UACC 903 or 1205 Lu cells in 0.2 mL of DMEM supplemented with 10% FBS. Cells were injected above both left and right rib cages of 3 to 4 week-old female Athymic-Foxn1$^{nu}$ nude mice (Harlan Sprague Dawley). Six days later, when a fully vascularized 50-75 mm³ tumor had formed, mice were randomly divided into 6 different groups: Group1 (DMSO); Group 2 (celecoxib, 10 mg/kg bodyweight); Group 3 (plumbagin, 0.5 mg/kg bodyweight); Group 4 (plumbagin, 1.0 mg/kg bodyweight); Group 5 (celecoxib 10 mg/kg bodyweight+plumbagin 0.5 mg/kg bodyweight); Group 6 (celecoxib 10 mg/kg bodyweight+plumbagin 1.0 mg/kg bodyweight) and treated by intraperitoneal (i.p.) injection of the indicated drug or drugs dissolved in DMSO on alternate days for 3-4 weeks (3 mice/group; 2 tumors/mouse). Body weight in grams and dimensions of developing tumors in mm³ were measured on alternate days.

The Combination of Celecoxib and Plumbagin Inhibited Melanoma Tumor Development

Figure 5:
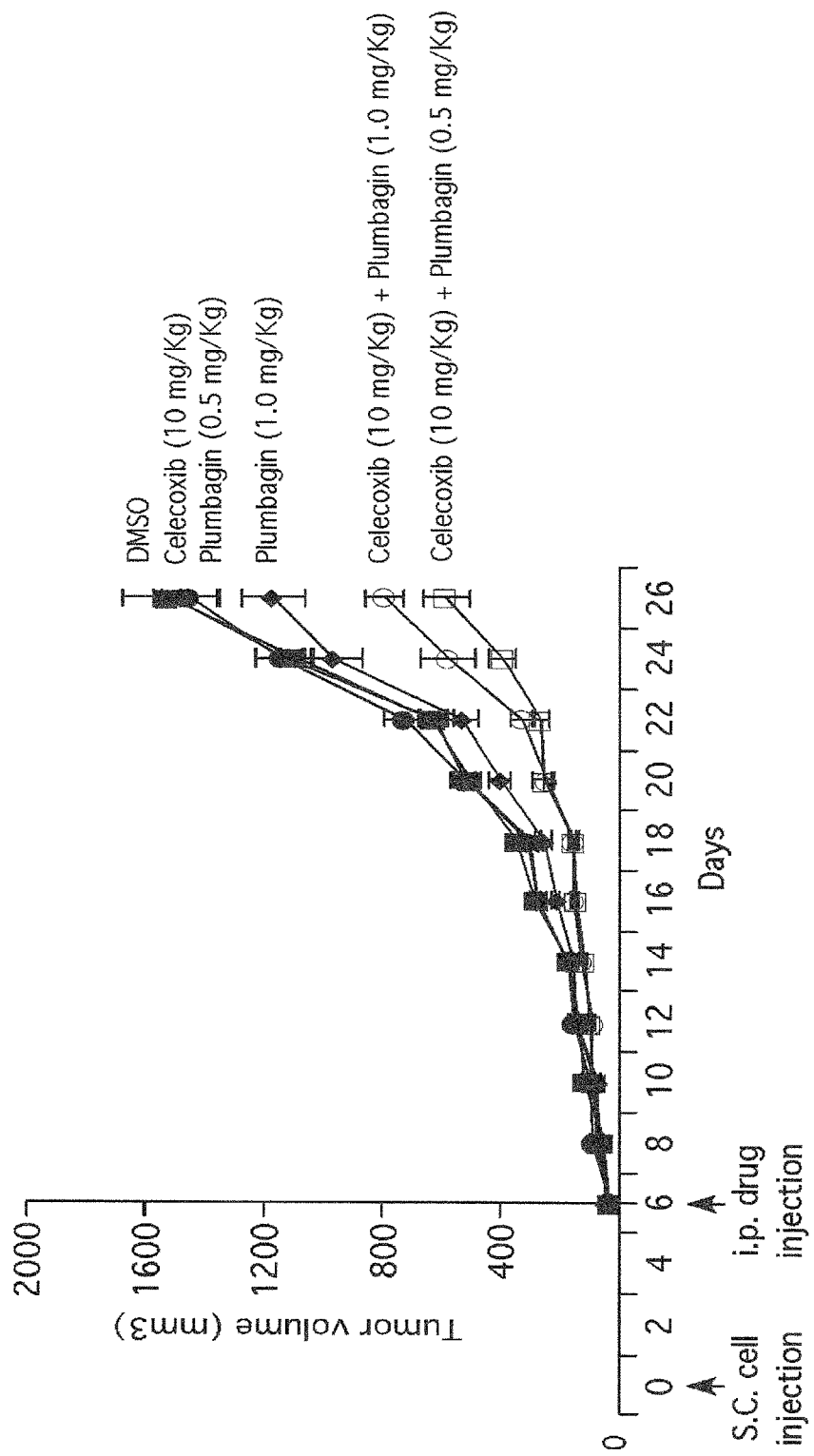
FIG. 5 is a graph showing in vivo synergy of celecoxib and plumbagin to inhibit UACC 903 melanoma cell xenograft tumors in nude mice, using plumbagin and celecoxib dissolved in DMSO and administered in a ratio of 1:10 or 1:20 in the amounts indicated.
Figure 6:
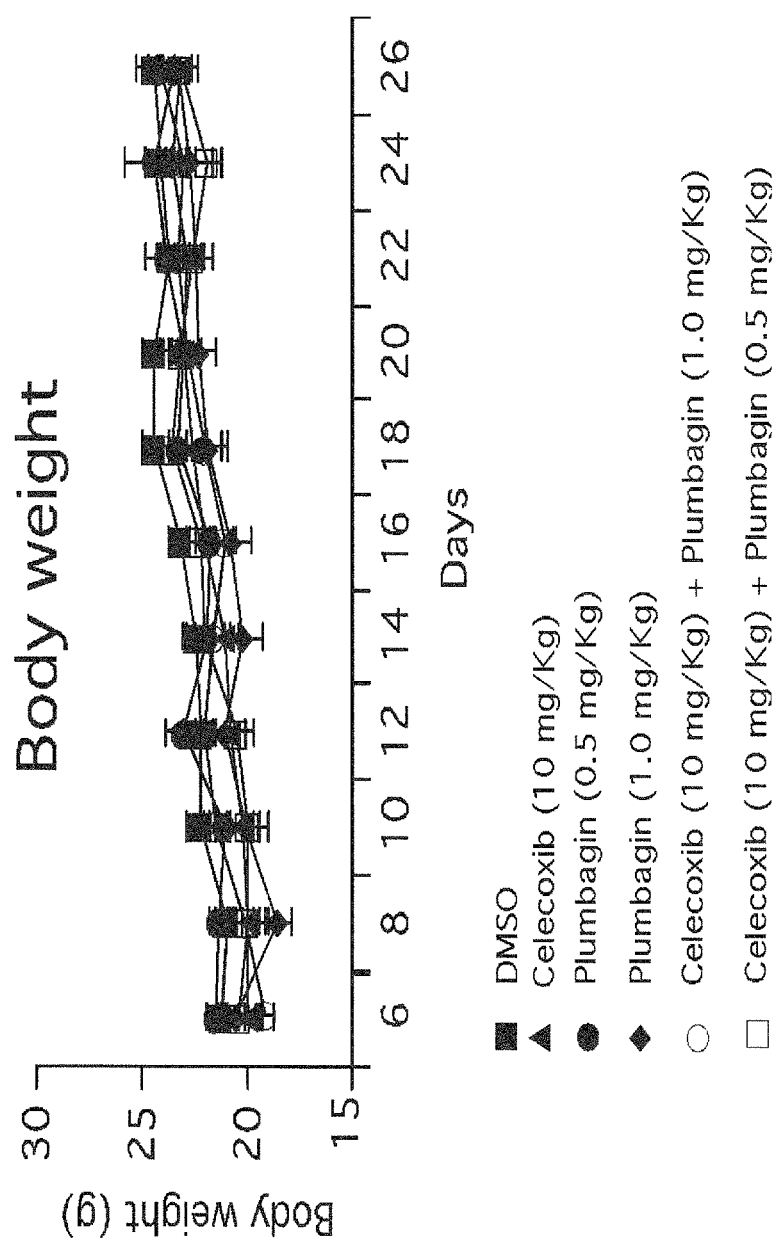
FIG. 6 is a graph showing that plumbagin:celecoxib at the 1:10 and plumbagin:celecoxib at the 1:20 drug ratio did not alter body weight of animals injected in the amounts indicated, suggesting negligible toxicity.
Figure 7:
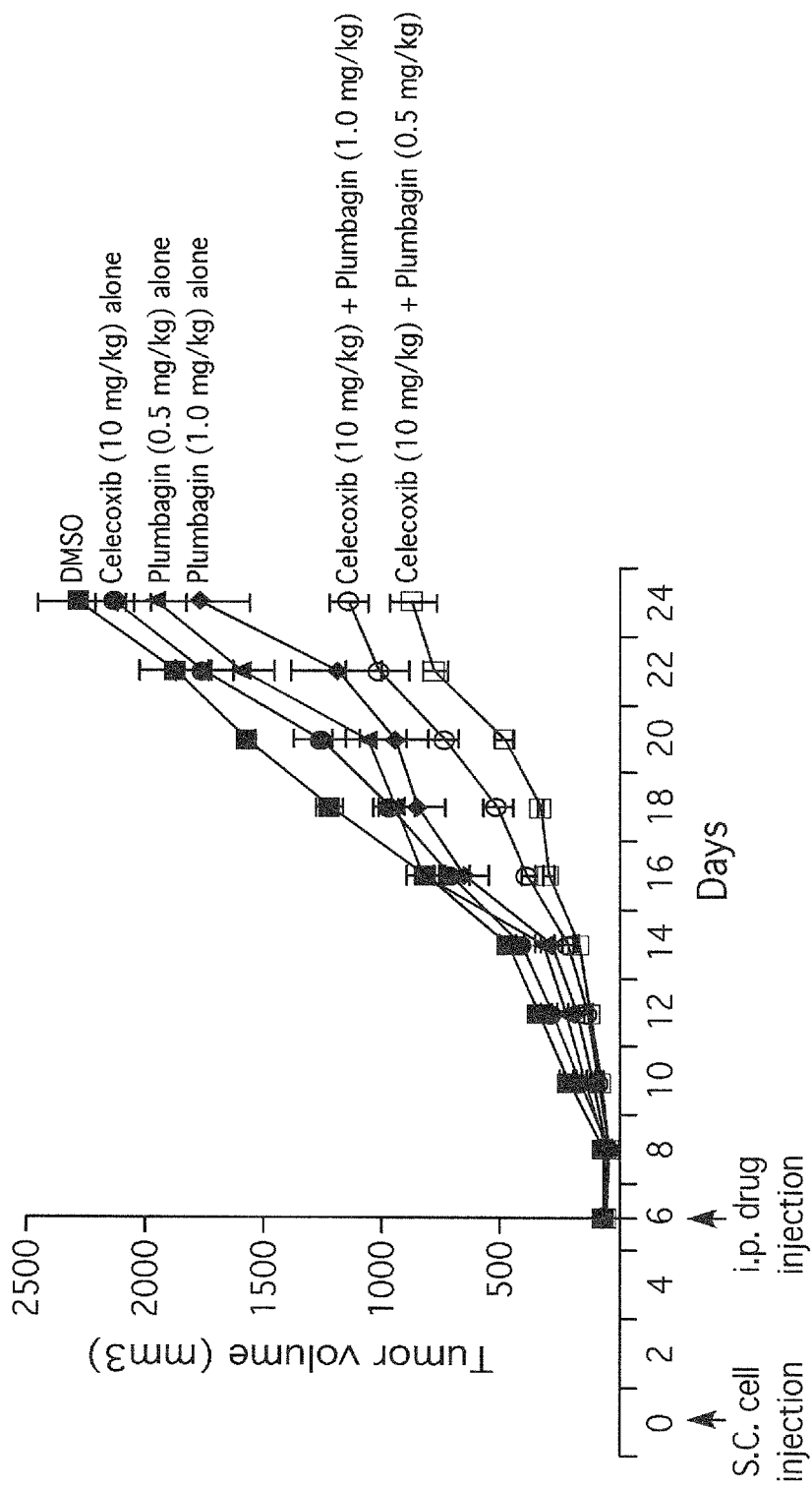
FIG. 7 is a graph showing in vivo synergy of celecoxib and plumbagin to inhibit 1205 Lu melanoma cell xenograft tumors in nude mice, using plumbagin and celecoxib dissolved in DMSO and administered in a ratio of 1:10 or 1:20 in the amounts indicated.
Figure 8:
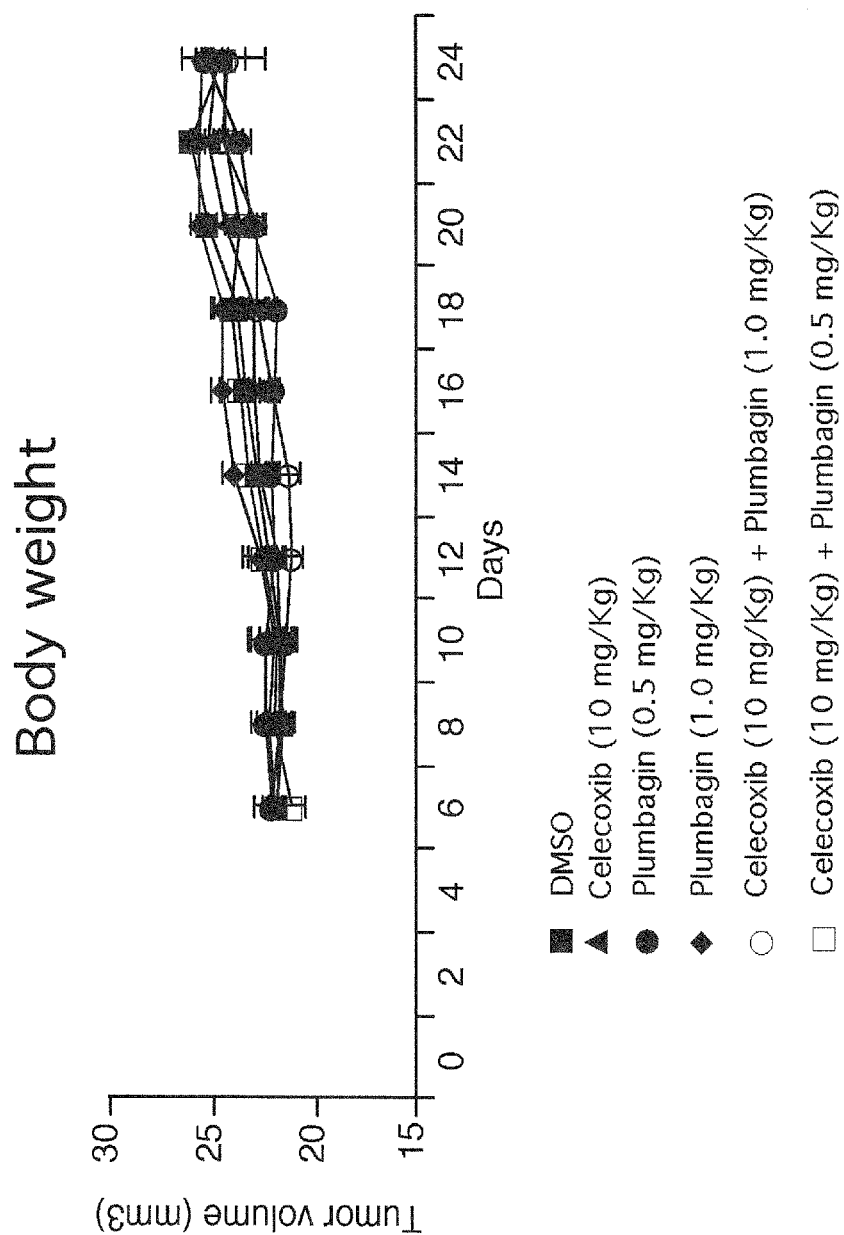
FIG. 8 is a graph showing that plumbagin:celecoxib at the 1:10 and plumbagin:celecoxib at the 1:20 drug ratio did not alter body weight of animals injected in the amounts indicated, suggesting negligible toxicity.

Plumbagin and celecoxib administered in a ratio of 1:20 decreased tumor development by up to 65-70% as shown in FIGS. 5 & 7, and plumbagin and celecoxib administered in a ratio of 1:10 decreased 50-55% in both UACC 903 and 1205 Lu cell lines, as shown in FIGS. 5 & 7, (P<0.001, two-way analysis of variance). FIG. 5 is a graph showing in vivo synergy of celecoxib and plumbagin to inhibit UACC 903 melanoma cell xenograft tumors in nude mice, using plumbagin and celecoxib dissolved in DMSO and administered in a ratio of 1:10 or 1:20 in the amounts indicated. FIG. 7 is a graph showing in vivo synergy of celecoxib and plumbagin to inhibit 1205 Lu melanoma cell xenograft tumors in nude mice, using plumbagin and celecoxib dissolved in DMSO and administered in a ratio of 1:10 or 1:20 in the amounts indicated. Plumbagin and celecoxib combination treatment at either the plumbagin:celecoxib 1:10 or plumbagin:celecoxib 1:20 drug ratio did not alter animal body weight, suggesting negligible toxicity as shown in FIGS. 6 & 8. These data suggest that combination of celecoxib and plumbagin inhibits xenografted melanoma tumor development without significant organ related toxicity. FIG. 6 is a graph showing that plumbagin:celecoxib at the 1:10 and plumbagin:celecoxib at the 1:20 drug ratio did not alter body weight of animals injected in the amounts indicated, suggesting negligible toxicity. FIG. 8 is a graph showing that plumbagin:celecoxib at the 1:10 and plumbagin:celecoxib at the 1:20 drug ratio did not alter body weight of animals injected in the amounts indicated, suggesting negligible toxicity.

Size and time match tumors treated with non-liposomal celecoxib, non-liposomal plumbagin for analysis of biological processes regulating tumor development.

Figure 9:
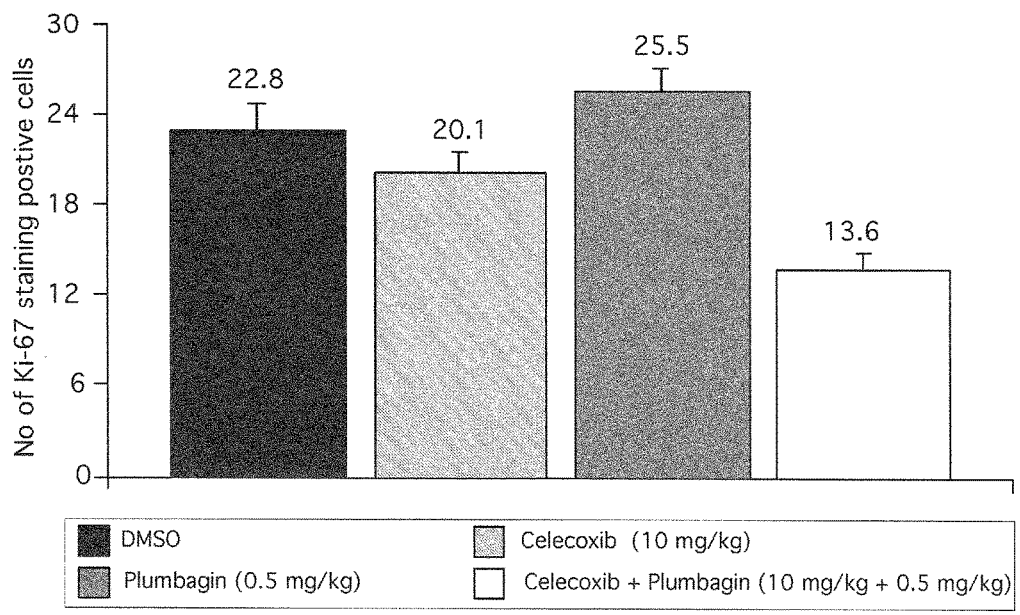
FIG. 9 is a graph showing results of an in vivo mechanistic study indicating that administration of plumbagin:celecoxib ratio in a ratio of 1:20 in the indicated amounts synergistically inhibits the proliferation potential of UACC 903 melanoma cells.

Mechanisms by which combination of non-liposomal celecoxib and non-liposomal plumbagin delayed tumor development was established by comparing size and time matched xenografted melanoma tumors treated with the single or combined agents. $2.5 \times 10^6$ UACC 903 cells were injected s.c. into nude mice, generating tumors of the same size developing at parallel time points. Six days later, mice were treated i.p. with DMSO, or celecoxib (10 mg/kg) or plumbagin (0.5 mg/kg) alone or in combination of celecoxib and plumbagin (10 mg/kg and 0.5 mg/kg), alternate days for up to 15 days. Tumors were harvested at days 11, 13 and 15 for comparison of rates of cellular proliferation by immunohistochemistry, see Sharma et al., Cancer Res., 2006, 66:8200-9; Huh et al. J Natl Cancer Inst., 2010, 102:1131-47; Stahl et al., Cancer Res., 2003, 63:2881-90 in time and size matched tumors treated with a plumbagin:celecoxib ratio of 1:20 compared with individual agents alone and vehicle control. Cell proliferation was measured using mouse anti-human Ki-67 staining from Pharmigen (San Diego, Calif.). Numbers of Ki-67 stained cells were quantified as the percentage of total cells in tumors using the IP Lab imaging software program. For all tumor analyses, a minimum of 4-6 different tumors with 4-6 fields per tumor section was analyzed and results represented as the average±SEM. Size and time matched tumors at day 13 were compared to identify statistically quantifiable differences in cell proliferation affected by combination treatment but not by the individual drugs singly as seen in FIG. 9. At day 13, a statistically significant approximately 50% reduction in proliferating cells was observed (P<0.001, two-way analysis of variance). FIG. 9 is a graph showing results of an in vivo mechanistic study indicating that administration of plumbagin:celecoxib ratio in a ratio of 1:20 in the indicated amounts synergistically inhibits the proliferation potential of UACC 903 melanoma cells.

Western Blot Analysis—Cells Treated with Non-Liposomal Drug Formulations.

Cell lysates from UACC 903 or 1205 Lu melanoma cells treated with 30-50 µmol/L celecoxib, 5 µmol/L plumbagin, or in combination (containing 30-50 µmol/L celecoxib+5 µmol/L plumbagin) for 24 hours followed by harvesting in RIPA lysis buffer containing Halt Protease & Phosphatase Inhibitor Cocktail (Thermo Scientific, Rockford, Ill.). Blots were probed with antibodies according to each supplier's recommendations: antibodies to pStat3 (Y705) cyclin D1, p27 and alpha-enloase and secondary antibodies conjugated with horseradish peroxidase from Santa Cruz Biotechnology (Santa Cruz, Calif.). Immunoblots were developed using the enhanced chemiluminescence (ECL) detection system (Thermo Fisher Scientific, Rockford, Ill.) or Supersignal West Femto Chemiluminescent Substrate (Thermo Fisher Scientific, Rockford, Ill.).

Celecoxib and plumbagin in combination inhibited the activity of cyclin D1 and STAT3 to retard melanoma tumor development.

Figure 10:
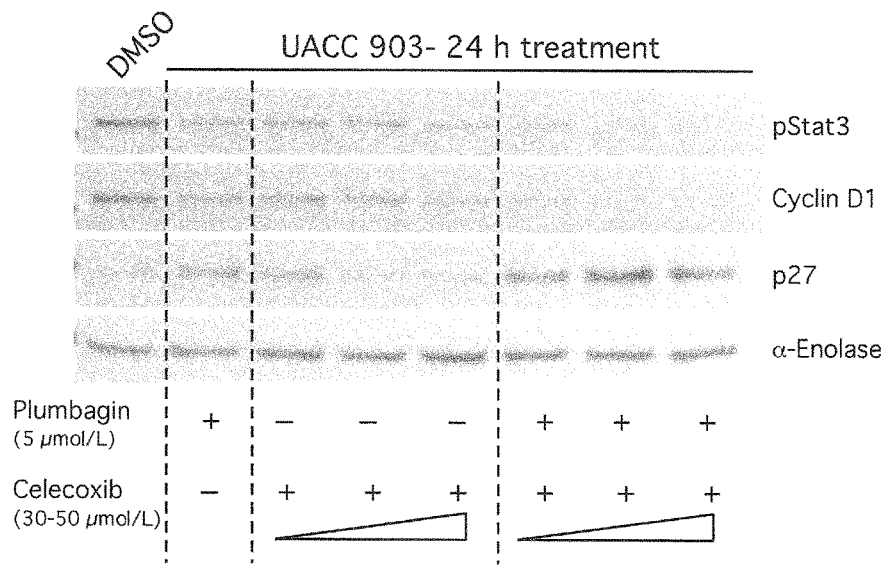
FIG. 10 is an image of a Western blot showing that celecoxib & plumbagin together synergistically inhibit UACC 903 melanoma cell growth by decreasing pSTAT3 levels and increasing p27 levels.

To identify the mechanism through which combination treatment decreased melanoma tumor development more effectively that either celecoxib or plumbagin alone, cells were treated with DMSO containing each agent alone or combined, FIG. 10. In UACC 903 melanoma cell line, decreased cyclin D1 and increased in p27 are observed, FIG. 10. Since cyclins are key to the functioning of the cyclin-cyclin dependent kinase complex in melanoma cells, reductions in the levels of these proteins, more prominent following treatment with combination than celecoxib or plumbagin alone, affects cell proliferation. In addition, the combination treatment also effectively decreased pStat3 levels, FIG. 10, indicating apoptosis appears to be mediated through decreased levels of active Stat3 in melanoma cell lines. FIG. 10 is an image of a Western blot showing that celecoxib & plumbagin together synergistically inhibit UACC 903 melanoma cell growth by decreasing pSTAT3 levels and increasing p27 levels.

Statistical Analysis for FIGS. 1-10.

Statistical analysis was performed using Prism 4.01 GraphPad Software and R version 2.15.1. One-way or Two-way Analysis Of Variance (ANOVA) was used for group wise comparisons, followed by the Tukey's or Bonferroni's post hoc tests. For comparison between two groups, Student t test was used. Results represent at least two to three independent experiments and are shown as averages±S.E.M. Results with a P value less than 0.05 (95% CI) were considered significant. Number of asterisks in these figures indicates the level of statistical significance as follows: *P<0.05, P<0.01, *P<0.001.

Thermal Stability of Celecoxib and Plumbagin.

Figure 11A:
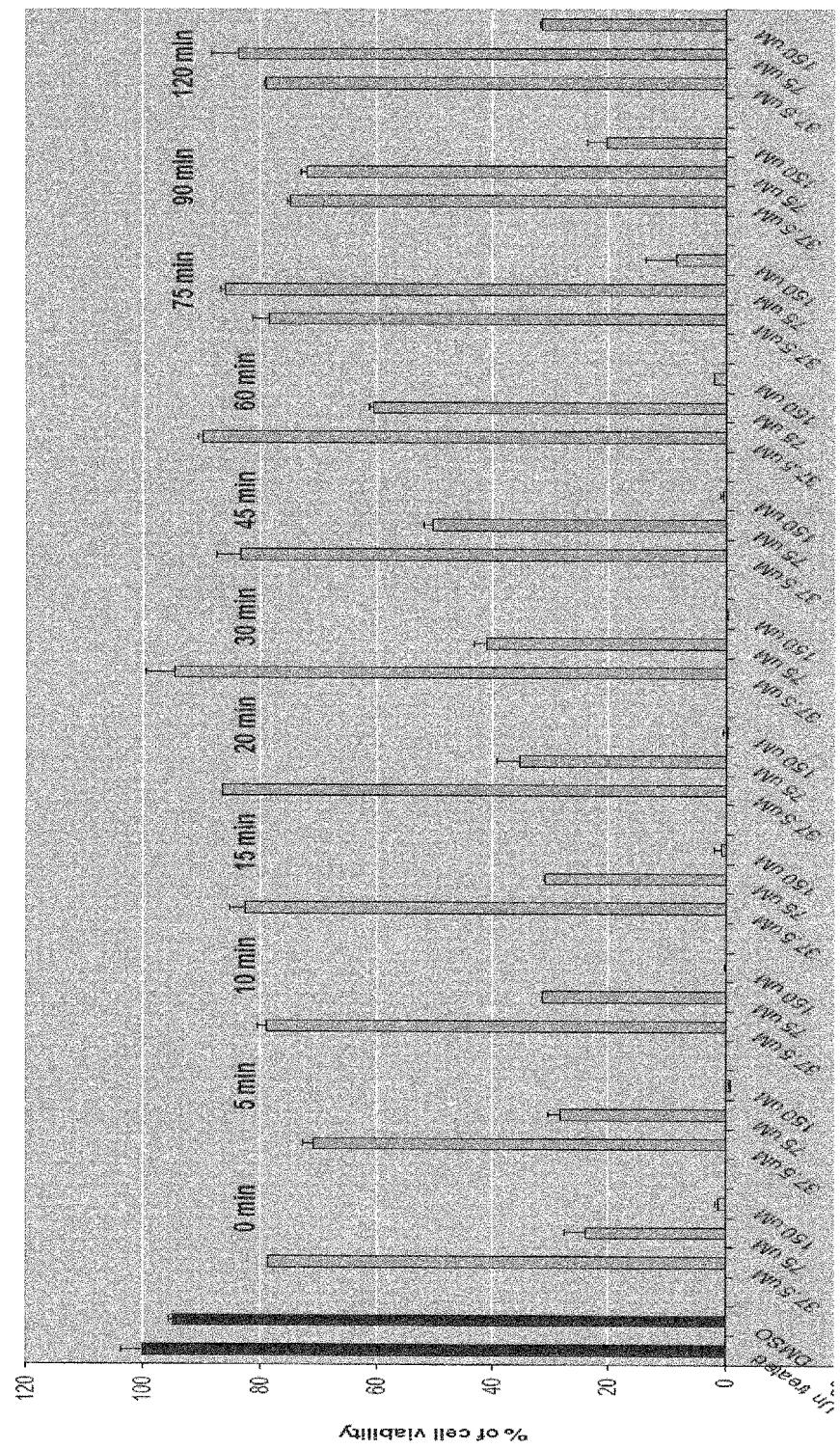
FIG. 11A is a graph showing that heating for a maximum of 20 minutes was found acceptable without decreasing the efficacy of celecoxib.
Figure 11B:
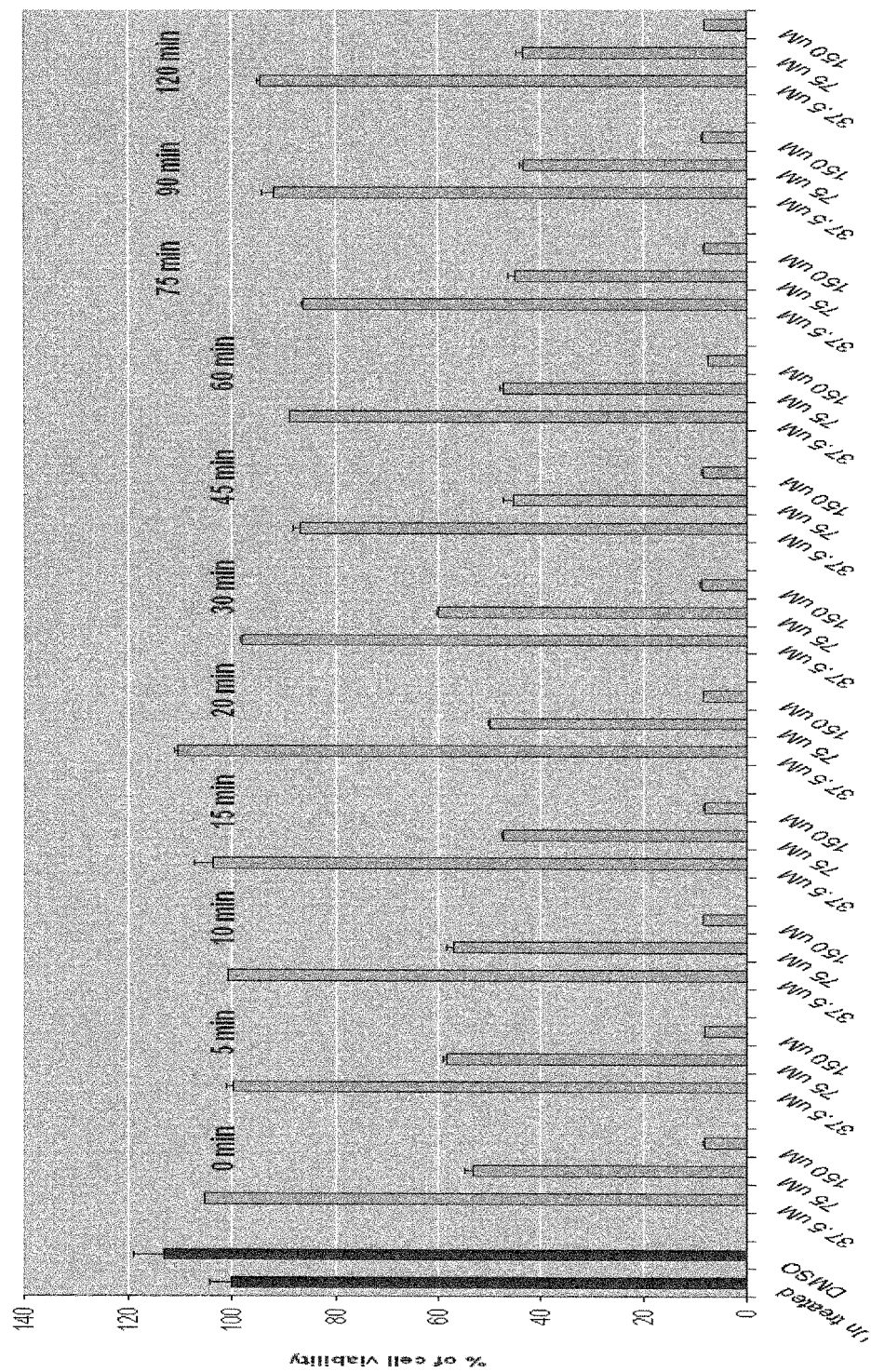
FIG. 11B is a graph showing that prolonged exposure of plumbagin to 60° C. temperature did not affect compound activity.

The thermal stability of celecoxib and plumbagin in DMSO solution was measured at various time points at 60° C. Efficacy of the heat treated compounds for killing UACC 903 melanoma cells was assessed using the MTS assay (Promega, Madison, Wis.). $5 \times 10^3$ UACC 903 cells per well in 100 µL of media were plated and grown in a 96-well plate for 48 hours and then treated with samples for 72 hours. Safe heating temperature for use during manufacture were determined by heating plumbagin or celecoxib for various time periods at 60° C. and then measuring efficacy for killing UACC 903 cells by MTS assay, as shown in FIGS. 11A and 11B. FIG. 11A is a graph showing that heating for a maximum of 20 minutes was found acceptable without decreasing the efficacy of celecoxib. FIG. 11B is a graph showing that prolonged exposure of plumbagin to 60° C. temperature did not affect compound activity.

Generation of Liposomes Containing Both Celecoxib and Plumbagin.

Figures 12, 13:
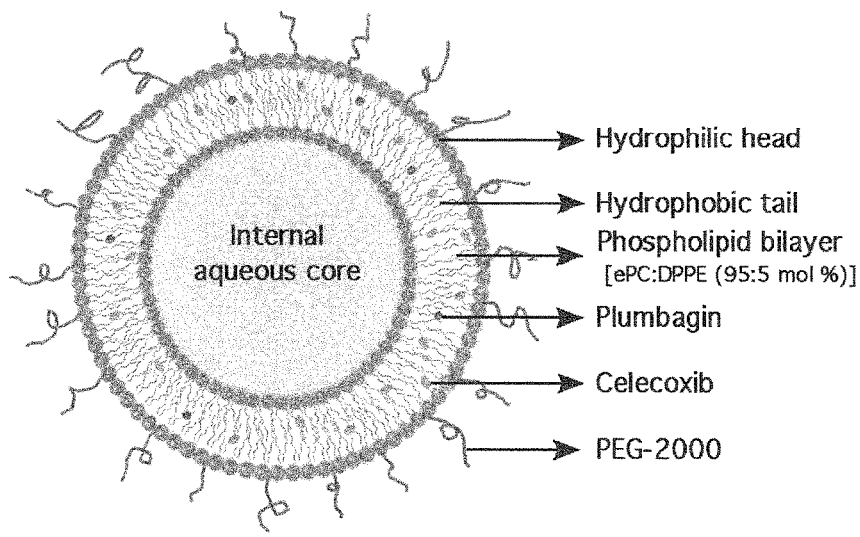
FIG. 12 is a schematic diagram of liposomes containing plumbagin and celecoxib.
FIG. 13 is a chart showing the average size and zeta potential of empty liposomes containing celecoxib, liposomes containing plumbagin and liposomes containing celecoxib and plumbagin, CelePlum-777.

To develop a clinically viable single agent that would contain plumbagin and celecoxib at 1:10 or 1:20 ratios that would inhibit melanoma cell viability in a synergistically acting manner, pegylated nanoliposomes containing plumbagin and celecoxib were created. FIG. 12 is a schematic diagram of liposomes containing plumbagin and celecoxib. Plumbagin and celecoxib drugs alone or in combination at a 1:10 or 1:20 plumbagin:celecoxib ratio, for example, plumbagin (0.05 mg/mL) and celecoxib (2 mg/mL) alone or in combination, were encapsulated into nanoliposomes called CelePlum-777 by combining L-α-phosphatidylcholine (ePC) and 1,2-dipalmitoyl-sn-glycero-3-phosphoethanolamine-N-[methoxy(polyethylene glycol)-2000] ammonium salt (DPPE-PEG-2000) in chloroform at 95:5 mol % for a final lipid concentration of 25 mg/mL (Avanti Polar Lipids Inc-Alabaster, Ala.)—these liposomes are used in examples described herein. Solvent was removed and mixture dried under nitrogen gas followed by resuspension in sterile saline or water at 60° C. with vortexing every 5 minutes over a 20 minutes period followed by extrusion at 60° C. through a 100-nm polycarbonate membrane using Avanti Mini Extruder (Avanti Polar Lipids Inc-Alabaster, Ala.). The particle size and charge characteristics were measured using a Malvern Zetasizer (Malvern Instruments, UK). Several nanoliposomal formulations were evaluated having variations in diameter, charge, membrane fluidity and surface hydration. Based on this evaluation, a novel lipid based PEGylated, liposomal system (95:5 mol % for ePC: DPPE: PEG-2000) containing both celecoxib and plumbagin was developed. The same lipid formulation was also found to be suitable for making a control empty liposome, one containing celecoxib alone or plumbagin alone and one containing both compounds at ratios of 1:10 or 1:20 plumbagin:celecoxib. The final solvent for the nanoliposomes was either water or saline. Using a Malvern Zetasizer Nano, Malvern Instruments, UK. The size and charge of the nanoliposomes was measured and indicated that the size in water of the nanoliposomes ranged from 66 to 81 urn and charge was −56 to −64 as shown in FIG. 13. The size in saline ranged from 68 to 74 nm and charge from −0.9 to −1.8 as shown in FIG. 13. Data represent averages of at least 3 independent experiments; bars; S.E.M. FIG. 13 is a chart showing the average size and zeta potential of empty liposomes containing celecoxib, liposomes containing plumbagin and liposomes containing celecoxib and plumbagin (CelePlum-777), synthesized as described.

Characterization of the liposomes generated as described containing both celecoxib and plumbagin.

Drug Loading of Liposomes.

The determination of encapsulation efficiency and release of plumbagin and celecoxib from liposomes was accomplished using 10 kDa Centricon® filters and centrifugation at 3750 rpm for 30 minutes, followed by estimating loading using UV-visible spectrophotometry.

Figure 14:
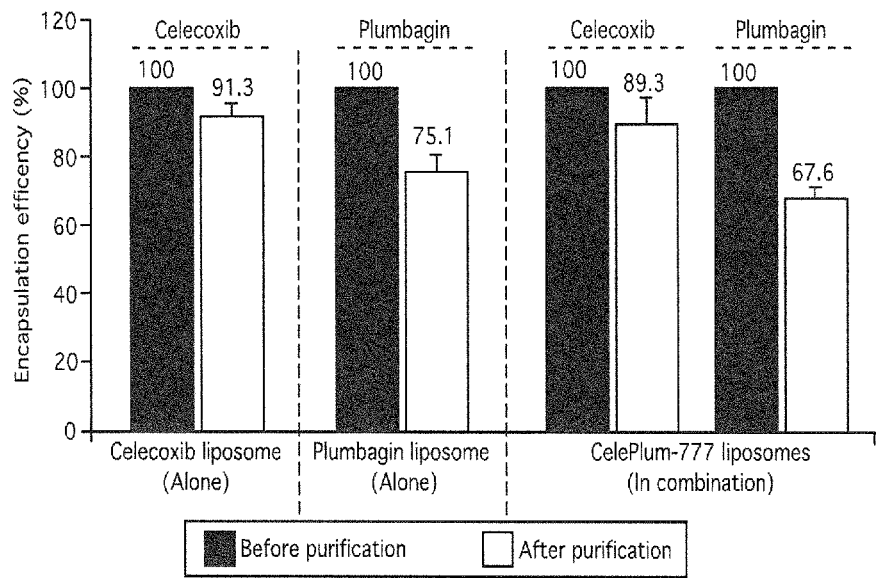
FIG. 14 shows graphs indicating efficiency of drug encapsulation into nanoliposomes containing celecoxib alone, plumbagin alone or both plumbagin and celecoxib.

Encapsulation of plumbagin and celecoxib singly or in combination at a ratio of 1:10 and 1:20 plumbagin:celecoxib in the nanoliposomal formulation was estimated by UV-visible spectrophotometry (SPECTRAmax M2 plate reader; Molecular devices, Sunnyvale, Calif.). Free drugs not incorporated into the nanoliposomes were separated using 10 kDa Centricon® filters (Millipore, Bedford, Mass.). This involved combining 0.5 mL of the nanoliposomal solution with 5 mL of hydration buffer followed by centrifugation at 3,750 rpm for 30 minutes. Next, 0.1 mL of purified nanoliposomal solution was combined with 1 mL of ethanol to destroy the nanoliposomal structure and release the drug into the solution. Following vortexing for 5 minutes, the precipitated lipids were separated following centrifugation at 10,000 rpm for 10 minutes. The supernatant was then used to measure the amount of each respective drug alone or in combination and concentrations calculated from standard curve of celecoxib or plumbagin ranging from 0.01 and 0.1 mg/mL. Ethanol was used as the reference blank. Percentage drug incorporated in the nanoliposome was calculated as the free drug(s)/total drug(s)×10. FIG. 14 shows graphs indicating efficiency of drug encapsulation into nanoliposomes containing celecoxib alone, plumbagin alone or both plumbagin and celecoxib. Loading was measured by UV-visible spectrophotometry using SPECTRAmax M2 plate reader (Molecular devices, Sunnyvale, Calif.). Data represent averages of at least 3 independent experiments; bars; S.E.M. The loading efficiency of drugs alone in celecoxib nanoliposomes and plumbagin nanoliposomes was found to be 91.3 and 75.1% respectively. For, the liposomes containing both celecoxib and plumbagin loading efficiency of individual drugs was 89.3% and 67.6% for celecoxib and plumbagin, respectively.

In Vitro Drug Release Kinetics from Liposomes Containing Both Celecoxib and Plumbagin.

Figure 15:
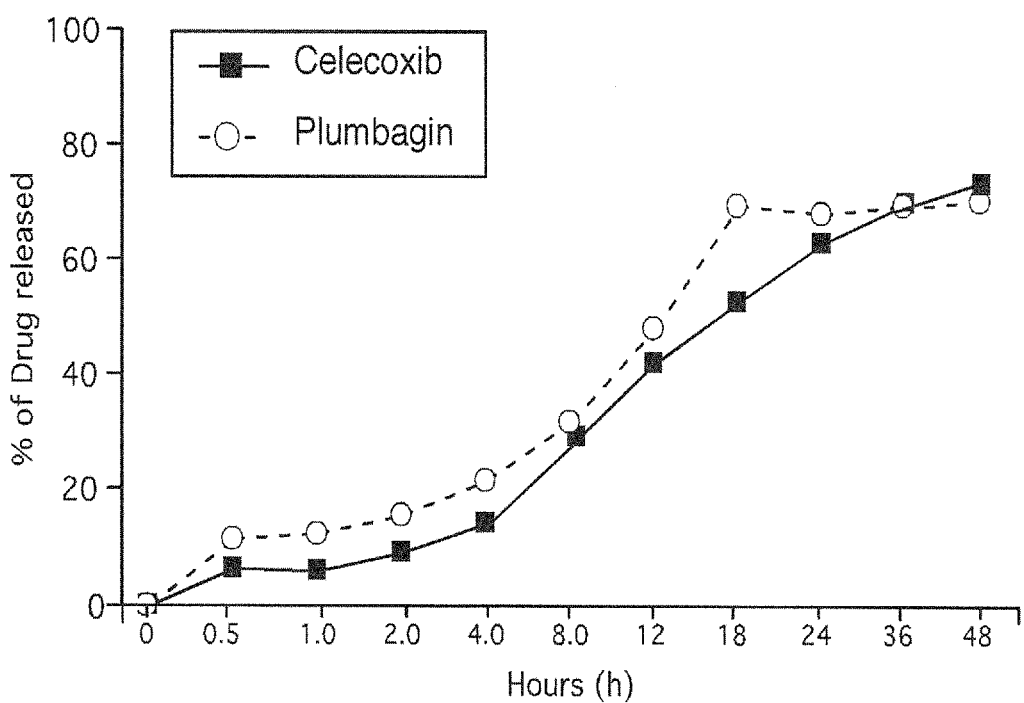
FIG. 15 is a graph showing the percentage of each drug released from liposomes containing both celecoxib and plumbagin over a period of 48 hours.

The in vitro release of celecoxib and plumbagin contained in liposomes containing both celecoxib and plumbagin was estimated at room temperature following dialysis through a molecular weight cut off 25 kDa membrane (Spectra Por, Los Angeles, Calif.). 1 mL purified liposomes containing both celecoxib and plumbagin in saline or water was placed into a dialysis membrane bag and suspended in 1 L of 10 mM reduced glutathione (GSH). 0.05 mL samples of the solution including liposomes containing both celecoxib and plumbagin contained in the dialysis bag was removed at 1, 2, 4, 8, 12, 18, 24, 36 and 48 hours and the amount of celecoxib and plumbagin released at each time point was estimated using UV-visible spectrophotometry with the SPECTRAmax M2 plate reader (Molecular devices, Sunnyvale, Calif.). Plumbagin was released occurred slowly during the first four hours and reached maximum of 69% by 18 hours. In contrast, celecoxib was released slowly during the first eight hours and reached maximum of 71% by 48 hours. FIG. 15 is a graph showing the percentage of each drug released from liposomes containing both celecoxib and plumbagin over a period of 48 hours.

Stability

Stability of liposomes containing both celecoxib and plumbagin stored at 4° C. was measured at various time intervals over 1 to 12 weeks. During this period no aggregation or precipitations of the nanoliposomes was observed. Assessing stability involved comparing size and charge using the Malvern Zetasizer Nano, (Malvern Instruments, UK) as well as assessing efficacy for killing UACC 903 melanoma cells using the MTS assay (Promega, Madison, Wis.). $5 \times 10^3$ UACC 903 cells per well in 100 μL of media were plated and grown in a 96-well plate for 48 hours and then treated with nanoliposomes containing each drug alone or in combination for 24 to 72 hours.

Figure 16:
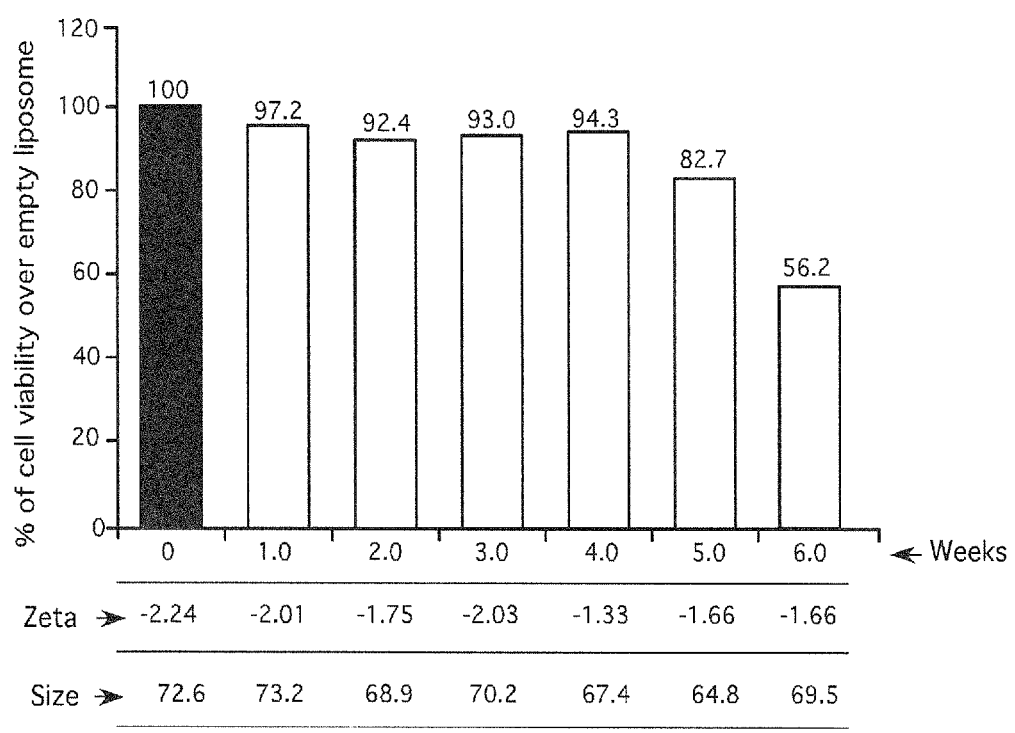
FIG. 16 is a graph showing stability of liposomes containing both celecoxib and plumbagin stored in sterile saline at 4° C. measured up to 6 weeks by comparing size, charge and efficacy for killing UACC 903 melanoma cells.

FIG. 16 is a graph showing stability of liposomes containing both celecoxib and plumbagin stored in sterile saline at 4° C. measured up to 6 weeks by comparing size, charge and efficacy for killing UACC 903 melanoma cells. Particle size and charge was measured using a Malvern Zetasizer Nano. During this period, the liposomes containing both celecoxib and plumbagin retained similar size and charge distributions as well as maintaining efficacy for killing UACC 903 melanoma cells as shown in FIG. 16. No aggregation or precipitation was observed during this period. Data in FIG. 16 represent averages of at least 3 independent experiments; bars; S.E.M.

Cell Viability, Proliferation, Apoptosis and Cell Cycle Analysis.

Viability of FF2441 fibroblast and UACC 903 and 1205 Lu melanoma cells following treatment with liposomes containing both celecoxib and plumbagin was measured by MTS assay (Promega, Madison, Wis.). MTS refers to 3-(4, 5-dimethylthiazol-2-yl)-5-(3-carboxymethoxyphenyl)-2-(4-sulfophenyl)-2H-tetrazolium) and assays using MTS to determine cell viability are well-known, see for example Barltrop, J. A. et al. (1991) Bioorg. Med. Chem. Lett., 1:611-4. Briefly, $5 \times 10^3$ melanoma or fibroblast cells were plated per well in 100 μl, of media and grown in 96-well plates for 48 hours. Cells were then treated with empty control liposomes, celecoxib liposomes (100 mol/L), plumbagin liposomes (5 μmol/L), or liposomes containing both celecoxib and plumbagin (containing 100 μmol/L celecoxib+5 μmol/L plumbagin) for 24, 48, or 72 hours before measuring cell viability.

Cellular Proliferation and Apoptosis Rates.

$5 \times 10^3$ UACC 903 and 1205 Lu melanoma cells were seeded in 96-well plates and treated as above. Percentage proliferating or apoptotic cells were quantified by a colorimetric cell proliferation ELISA BrdU kit (Roche Applied Sciences, Indianapolis, Ind.) or fluorimetric Apo-ONE Homogenous caspase-3/7 assay kit (Promega, Madison, Wis.).

Cell Cycle Analysis.

Cells in each phase of the cell cycle were calculated by growing $7.5 \times 10^5$ UACC 903 or 1205 Lu melanoma cells in 100-mm culture dishes for 48 hours followed by treatment with empty control liposome, celecoxib liposome (100 μmol/L), plumbagin liposome (5 mol/L), or liposomes containing both 100 μmol/L celecoxib, 5 μmol/L plumbagin for 24 hours. Total floating and adherent cells were collected following trypsinization and stained with 1 mL of a propidium iodide solution containing 0.1 mg/mL propidium iodide (Sigma, St Louis, Mo.), 0.02 mg/mL Ribonuclease A (Roche, Indianapolis, Ind.), 1 mg/mL sodium citrate, and 0.3% Triton-X-100 in 1×PBS. Stained cells were analyzed on a BD FACSCalibur and results analyzed utilizing ModFit LT software (Verity Software House, Topsham, Me.).

Liposomes Containing Both Celecoxib and Plumbagin Decreased Cellular Proliferation, Triggered Apoptosis and Arrested Melanoma Cells in the $G_2/M$ Phase of the Cell Cycle.

Figure 17A:
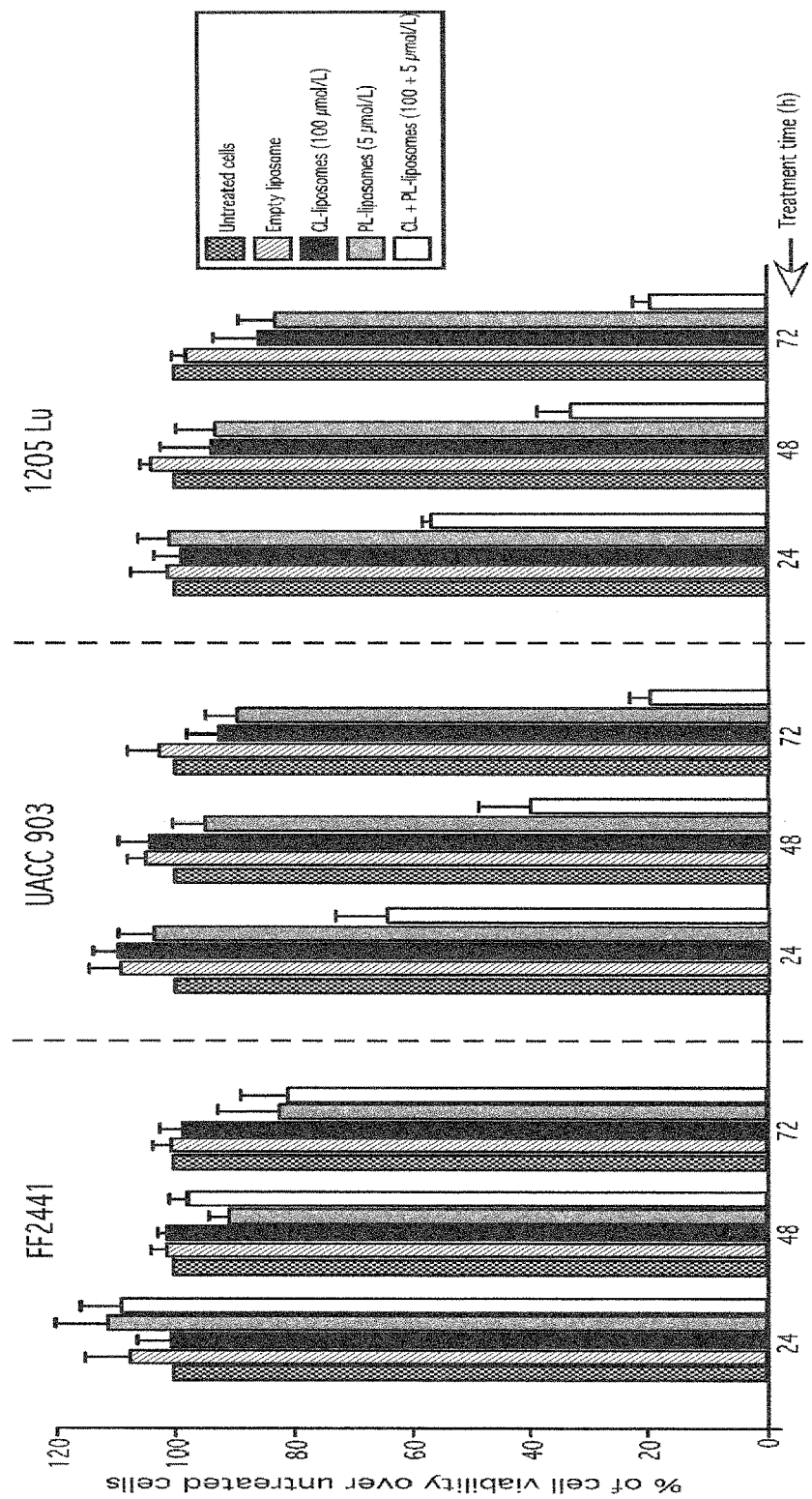
FIG. 17A shows graphs comparing the responsiveness of fibroblasts or melanoma cells to liposomes containing celecoxib (CL liposomes, 100 µmol/L celecoxib), liposomes containing plumbagin (PL liposomes, 5 µmol/L plumbagin) or liposomes containing both celecoxib and plumbagin (CL+PL liposomes, 100 µmol/L celecoxib+5 µmol/L plumbagin)

Efficacy of liposomes containing both celecoxib and plumbagin at the 1:20 ratio of plumbagin (5 μmol/L):celecoxib (100 μmol/L) for killing cultured melanoma cells compared to normal cells was examined by treating FF2441 human fibroblasts or UACC 903 or 1205 Lu melanoma cells with empty nanoliposomes or those containing celecoxib, plumbagin or both agents for 24, 48 and 72 hours and then assessing cell survival by MTS assay. FIG. 17A shows graphs comparing the responsiveness of fibroblasts or melanoma cells to liposomes containing celecoxib (CL liposomes, 100 μmol/L celecoxib), liposomes containing plumbagin (PL liposomes, 5 μmol/L plumbagin) or liposomes containing both celecoxib and plumbagin (CL+PL liposomes, 100 μmol/L celecoxib+5 μmol/L plumbagin). FF2441 human fibroblasts or UACC 903 or 1205 Lu melanoma cells were treated with empty control liposome, celecoxib liposome (100 mol/L), plumbagin liposome (5 μmol/L), or liposomes containing both celecoxib and plumbagin (100 μmol/L, celecoxib, 5 μmol/L, plumbagin) for 24, 48 and 72 hours and cell survival assessed by MTS assay. Negligible changes were seen in the proliferative potential of the fibroblasts or for melanoma cells treated with the empty nanoliposomes or those containing celecoxib or plumbagin over the 72-hour treatment period. In contrast, treatment with liposomes containing both celecoxib and plumbagin led to 40, 60 and 80% inhibition at 24, 48 and 72 hours, respectively, as shown in FIG. 17A. Data represent averages of at least 3 independent experiments; bars; S.E.M.

Figure 17B:
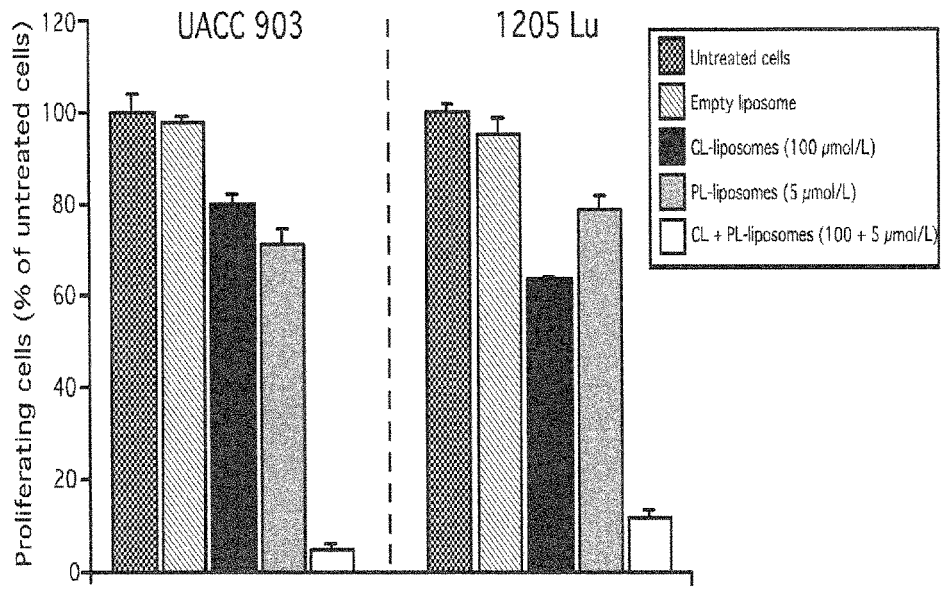
FIG. 17B shows graphs showing the decrease in rates of cell proliferation over untreated UACC 903 and 1205 Lu melanoma cells when such cells are treated with liposomes containing celecoxib and plumbagin (CL+PL-liposomes—100 µmol/L+5 µmol/L) compared to treatment with empty liposomes, liposomes containing celecoxib (CL-liposomes—100 µmol/L) or liposomes containing plumbagin (PL-liposomes—5 µmol/L)

To unravel the cellular processes leading to growth inhibition of cultured cells after treatment with liposomes containing both celecoxib and plumbagin compared to nanoliposomes containing each agent alone, the rates of cell proliferation, apoptosis, and the percentage of cells in the various phases of the cell cycle were measured after 72 hours of treatment. FIG. 17B shows graphs indicating rates of cell proliferation following treatment with liposomes containing both celecoxib and plumbagin. While treatment with nanoliposomes containing celecoxib or plumbagin alone reduced melanoma cell proliferation from 20 to 35%, the nanoparticles containing both agents decreased cell survival by 90 to 95% as shown in FIG. 17B. Data represent averages of at least 3 independent experiments; bars; S.E.M.

Figure 17C:
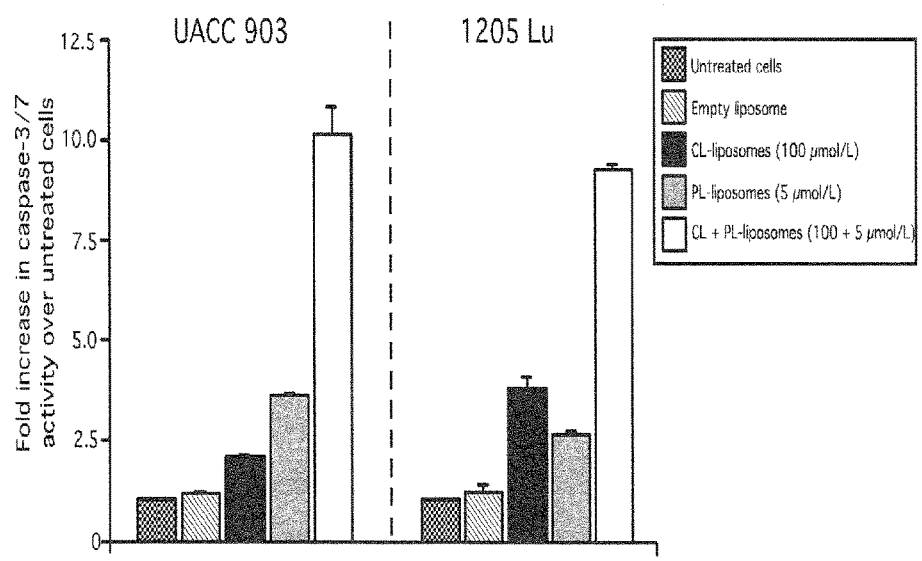
FIG. 17C is a graph showing the increase in caspase-3/7 activity over untreated UACC 903 and 1205 Lu melanoma cells when such cells are treated with liposomes containing celecoxib and plumbagin (CL+PL-liposomes—100 µmol/L+5 mol/L) compared to treatment with empty liposomes, liposomes containing celecoxib (CL-liposomes—100 µmol/L) or liposomes containing plumbagin (PL-liposomes—5 µmol/L)

Similar changes were seen in apoptosis rates, where the nanoliposomes containing celecoxib or plumbagin alone increased levels by 1 to 3 fold compared to 8 to 10-fold increases when the melanoma cells were treated with liposomes containing both celecoxib and plumbagin as shown in FIG. 17C. FIG. 17C is a graph showing the increase in caspase-3/7 activity over untreated UACC 903 and 1205 Lu melanoma cells when such cells are treated with liposomes containing celecoxib and plumbagin (CL+PL-liposomes—100 μmol/L+5 μmol/L) compared to treatment with empty liposomes, liposomes containing celecoxib (CL-liposomes—100 μmol/L) or liposomes containing plumbagin (PL-liposomes—5 μmol/L). Data represent averages of at least 3 independent experiments; bars; S.E.M.

Figure 17D:
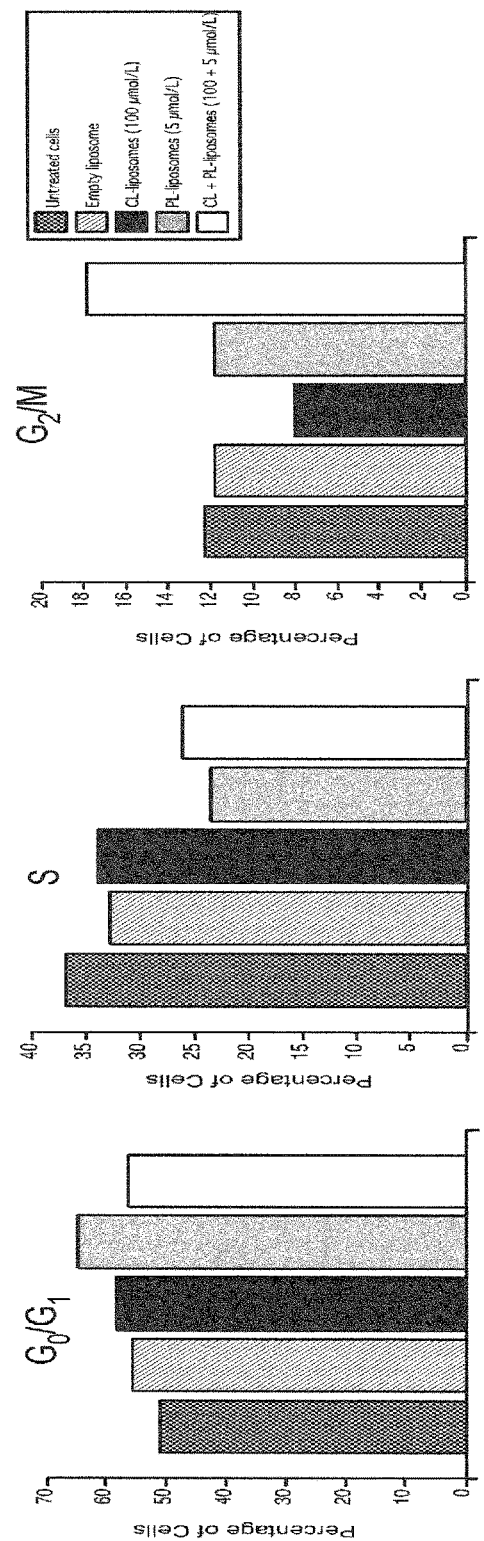
FIG. 17D is a set of graphs showing increases in the $G_2$/M cell populations, with a corresponding decrease in the S phase population of UACC 903 melanoma cells following 24 hour treatment with empty control liposomes, celecoxib liposomes (CL-liposomes 100 µmol/L celecoxib), plumbagin liposomes (PL liposomes 5 µmol/L plumbagin), or liposomes containing both celecoxib and plumbagin (CL+PL liposomes 100 µmol/L celecoxib+5 µmol/L plumbagin)

Melanoma cells were treated with empty control liposomes, celecoxib liposomes (CL-liposomes 100 μmol/L celecoxib), plumbagin liposomes (PL liposomes 5 μmol/L plumbagin), or liposomes containing both celecoxib and plumbagin (CL+PL liposomes 100 μmol/L celecoxib+5 μmol/L plumbagin) for 24 hours. Cells were stained with propidium iodide solution, run on a BD FACSCalibur and results analyzed utilizing ModFit LT software. Cell cycle analysis of propidium iodide stained UACC 903 cells following 24 hour treatment showed increases in the $G_2/M$ cell populations, with a corresponding decrease in the S phase population, as shown in FIG. 17D. FIG. 17D is a set of graphs showing increases in the $G_2/M$ cell populations, with a corresponding decrease in the S phase population of UACC 903 melanoma cells following 24 hour treatment with empty control liposomes, celecoxib liposomes (CL-liposomes 100 μmol/L, celecoxib), plumbagin liposomes (PL liposomes 5 μmol/L plumbagin), or liposomes containing both celecoxib and plumbagin (CL+PL liposomes 100 μmol/L celecoxib+5 μmol/L, plumbagin). Data represent averages of at least 3 independent experiments.

Tumorigenicity Assessments—Liposomes.

Tumor kinetics were measured by subcutaneous injection of $1 \times 10^6$ UACC 903 or 1205 Lu cells in 0.2 mL of DMEM supplemented with 10% FBS. Cells were injected above both left and right rib cages of 3 to 4 week-old female Athymic-Foxn1$^{nu}$ nude mice (Harlan Sprague Dawley). Six days later, when a fully vascularized 50-75 mm³ tumor had formed, mice were randomly divided into 7 different groups: Group1 (empty liposomes (no drug) reconstituted in saline or water); Group 2 (celecoxib, 15 mg/kg bodyweight reconstituted in saline or water); Group 3 (plumbagin, 0.75 mg/kg bodyweight reconstituted in saline or water); Group 4 (plumbagin, 1.5 mg/kg bodyweight reconstituted in saline or water); Group 5 (celecoxib 15 mg/kg bodyweight+plumbagin 0.75 mg/kg bodyweight reconstituted in saline or water); Group 6 (celecoxib 15 mg/kg bodyweight+plumbagin 1.5 mg/kg bodyweight reconstituted in saline or water) and treated intravenously on alternate days for 3-4 weeks (3 mice/group; 2 tumors/mouse). Body weight in grams and dimensions of developing tumors in mm³ were measured on alternate days.

Size and Time Match Tumors for Analysis of Biological Processes Regulating Tumor Development.

The mechanism by which liposomes containing both celecoxib and plumbagin delayed tumor development was established by comparing size and time matched xenografted melanoma tumors treated with empty control liposome or liposomes containing single or combined agents. 2.5×10⁶ 1205 Lu cells were injected s.c. into nude mice, generating tumors of the same size developing at parallel time points. Six days later, mice were treated i.v. with empty liposomes, nanoliposomes containing plumbagin or celecoxib alone or nanoliposomes containing both plumbagin and celecoxib, daily for up to 15 days. Tumors were harvested at days 11, 13 and 15 for comparison of rates of cellular proliferation, apoptosis and vessel density by immunohistochemistry. Cell proliferation was measured using mouse anti-human Ki-67 staining from Pharmigen (San Diego, Calif.). Apoptosis rates were determined using "terminal deoxynucleotidyl transferase-mediated dUTP nick end labeling (TUNEL)" TMR Red Apoptosis kit from Roche (Mannheim, Germany). Vessel density indicative of angiogenesis was measured using a purified rat anti-mouse CD31 (PECAM-1) monoclonal antibody for immunostaining (Pharmingen). Number of Ki-67 or TUNEL stained cells were quantified as the percentage of total cells in tumors using the IP Lab imaging software program. Areas containing vessels were quantified and compared between tumor sections. For all tumor analyses, a minimum of 4-6 different tumors with 4-6 fields per tumor section was analyzed and results represented as the average±SEM.

Toxicity Assessments and Histological Analysis of Organs.

Animals from tumorigenicity assessment experiment were used to assess the toxicity associated with individual or combined agents. At the end of treatment, blood was collected from each euthanized animal in a serum separator tube with lithium heparin (BD Microtainer) following cardiac puncture and analyzed for levels of GLU (Glucose), BUN (Blood urea nitrogen), CREA (Creatinine), Phosphate, TP (Total Protein), CAL (Calcium), GLO (Globulin), ALT (Alanine aminotransferase), ALKP (Alkaline phosphatase), TBIL (Total bilirubin), CHOL (Total cholesterol), TRIG (Total triglyceride), AST (Aspartate aminotransferase) and AMY (Amylase) to ascertain possible vital organs such as liver, heart, kidney, and pancreas related toxicity. A portion of liver, heart, kidney, pancreas, spleen, intestine and stomach tissue from each animal was formalin-fixed and paraffin-embedded to examine changes in cell morphology and tissue organization following hematoxylin/eosin (H&E) staining.

Statistical Analysis for FIGS. 13-19.

Statistical analysis was performed using Prism 4.0 GraphPad Software. One-way or Two-way Analysis Of Variance (ANOVA) was used for group wise comparisons, followed by the Tukey's or Bonferroni's post hoc tests. For comparison between two groups, Student t test (2-tailed) was used. Results represent at least two to three independent experiments and are shown as averages±S.E.M. Results with a P value less than 0.05 (95% CI) were considered significant. Sample sizes and number of times experiments were repeated are indicated in the Examples. Number of asterisks in the figures indicates the level of statistical significance as follows: *, P<0.05; , P<0.01; *, P<0.001.

Liposomes Containing Both Celecoxib and Plumbagin Inhibited Melanoma Tumor Development with Negligible Major Organ Related Toxicity.

Figure 18A:
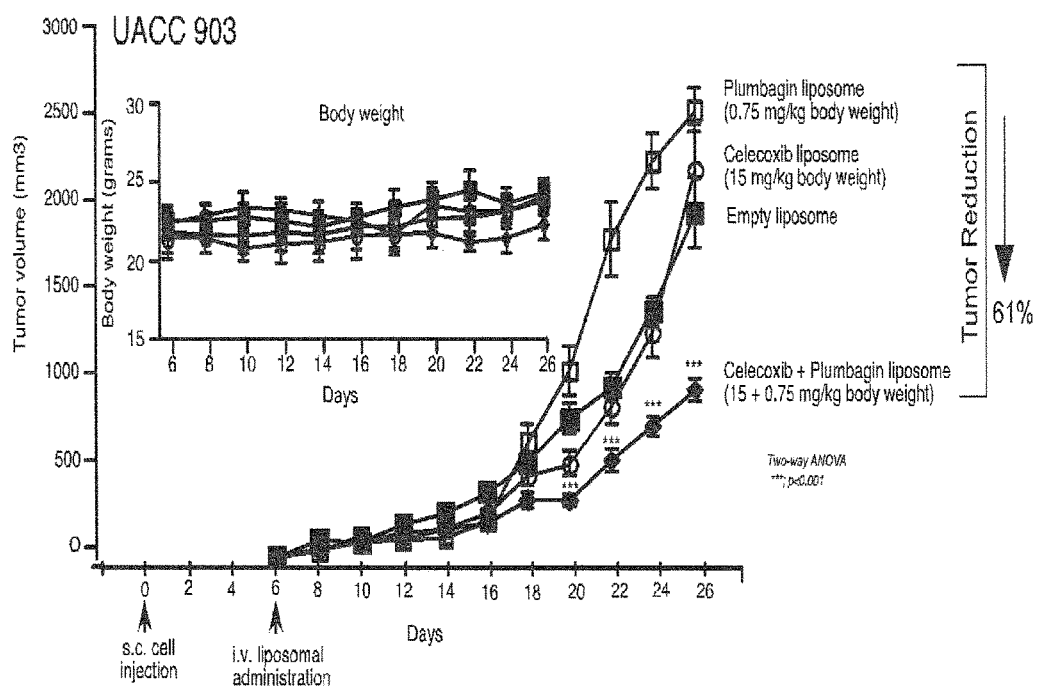
FIG. 18A is a set of graphs showing that administration of liposomes containing both celecoxib and plumbagin at a 1:20 plumbagin:celecoxib ratio in the indicated dosage administered in water to nude mice having UACC 903 melanoma xenograft tumors decreased tumor development compared to the same liposomes containing celecoxib or plumbagin alone at the indicated dosage and compared to the same liposomes without any drug, P<0.001, two-way analysis of variance, and with negligible change in body weight over the treatment period as shown in the inset.
Figure 18B:
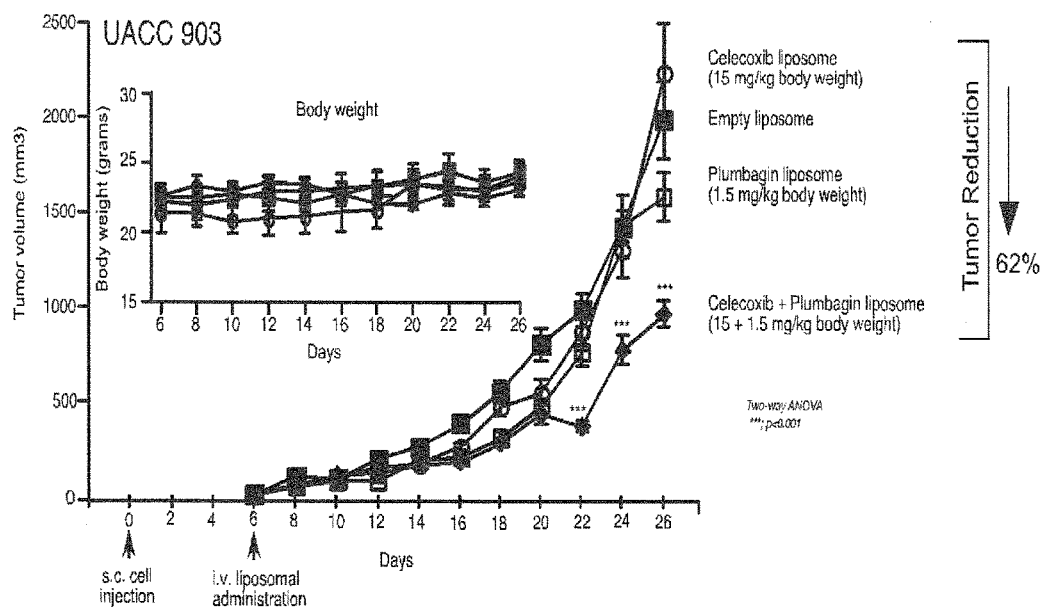
FIG. 18B is a set of graphs showing that administration of liposomes containing both celecoxib and plumbagin at a 1:10 plumbagin:celecoxib ratio in the indicated dosage administered in water to nude mice having UACC 903 melanoma xenograft tumors decreased tumor development compared to the same liposomes containing celecoxib or plumbagin alone at the indicated dosage and compared to the same liposomes without any drug, P<0.001, two-way analysis of variance, and with negligible change in body weight over the treatment period as shown in the inset.
Figure 18C:
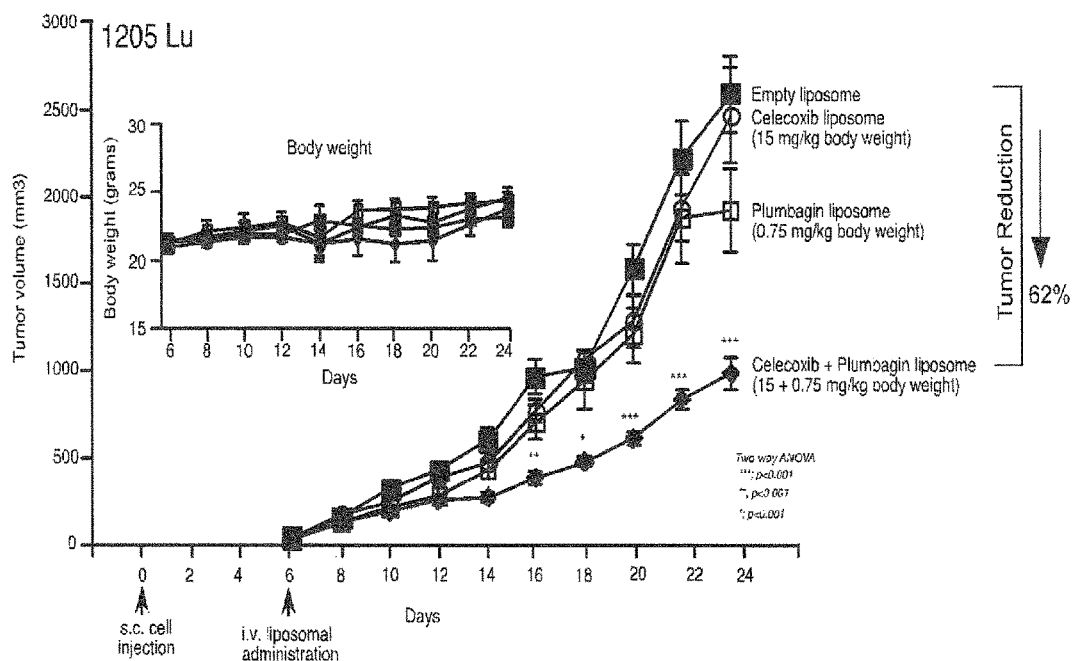
FIG. 18C is a set of graphs showing that administration of liposomes containing both celecoxib and plumbagin at a 1:20 plumbagin:celecoxib ratio in the indicated dosage administered in water to nude mice having 1205 Lu melanoma xenograft tumors decreased tumor development compared to the same liposomes containing celecoxib or plumbagin alone at the indicated dosage and compared to the same liposomes without any drug, P<0.001, two-way analysis of variance, and with negligible change in body weight over the treatment period as shown in the inset.
Figure 18D:
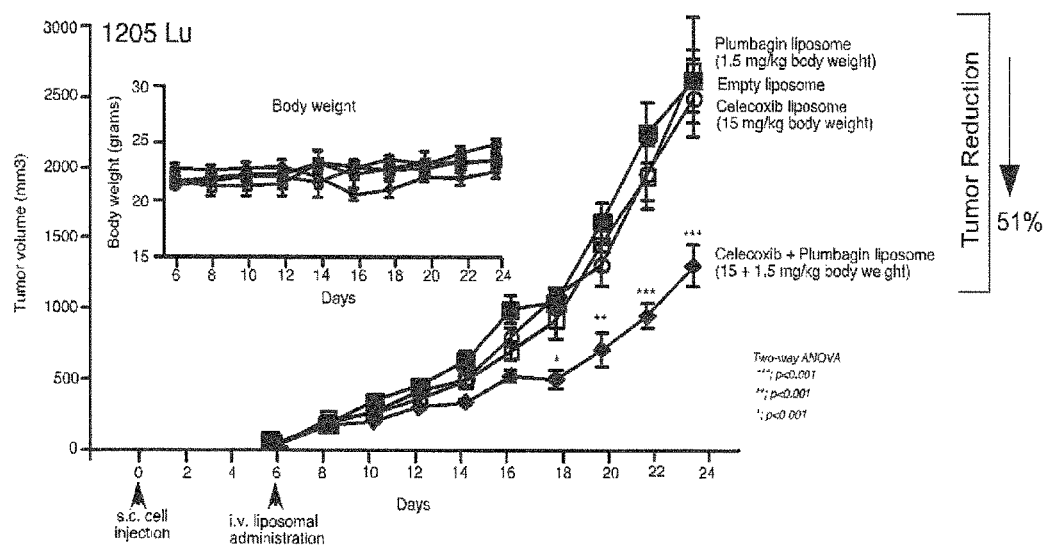
FIG. 18D is a set of graphs showing that administration of liposomes containing both celecoxib and plumbagin at a 1:10 plumbagin:celecoxib ratio in the indicated dosage administered in water to nude mice having 1205 Lu melanoma xenograft tumors decreased tumor development compared to the same liposomes containing celecoxib or plumbagin alone at the indicated dosage and compared to the same liposomes without any drug, P<0.001, two-way analysis of variance, and with negligible change in body weight over the treatment period as shown in the inset.
Figure 18E:
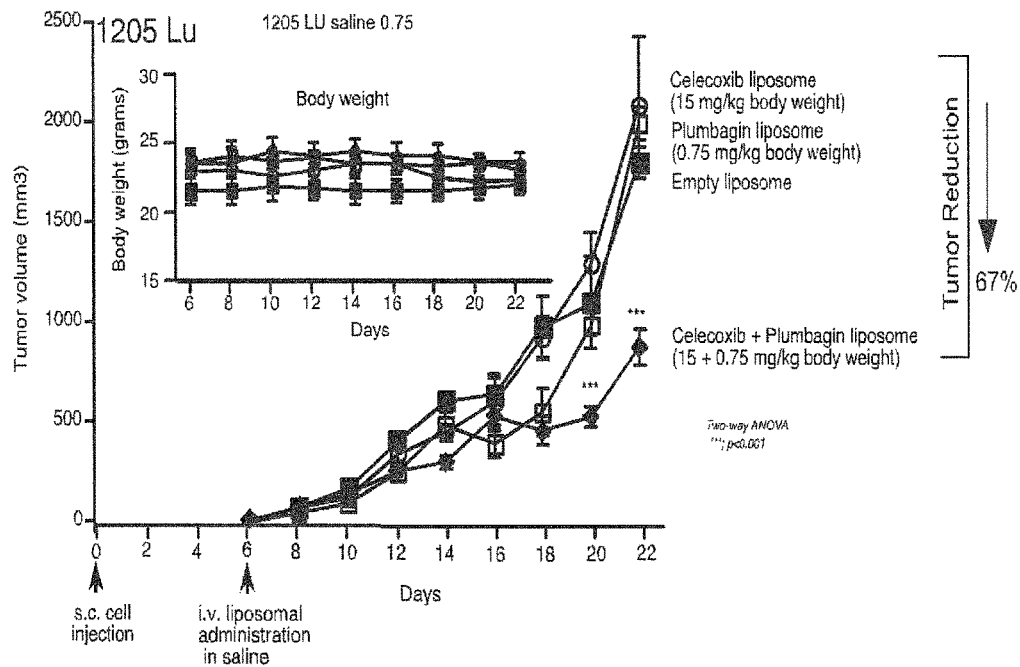
FIG. 18E is a set of graphs showing that administration of liposomes containing both celecoxib and plumbagin at a 1:20 plumbagin:celecoxib ratio in the indicated dosage administered in saline to nude mice having 1205 Lu melanoma xenograft tumors decreased tumor development compared to the same liposomes containing celecoxib or plumbagin alone at the indicated dosage and compared to the same liposomes without any drug, P<0.001, two-way analysis of variance, and with negligible change in body weight over the treatment period as shown in the inset.
Figure 18F:
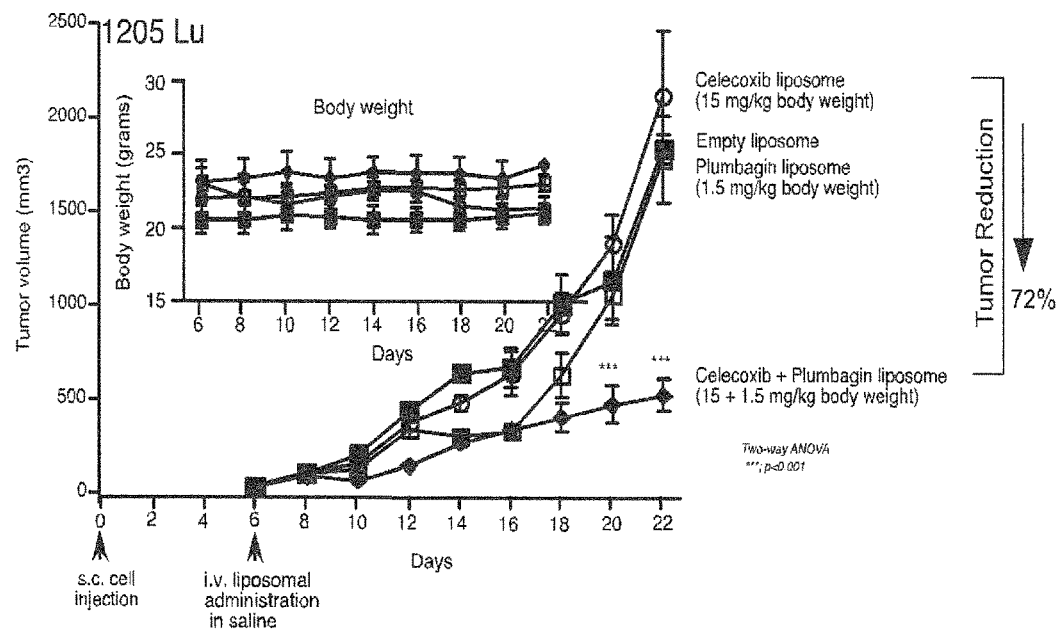
FIG. 18F is a set of graphs showing that administration of liposomes containing both celecoxib and plumbagin at a 1:10 plumbagin:celecoxib ratio in the indicated dosage administered in saline to nude mice having 1205 Lu melanoma xenograft tumors decreased tumor development compared to the same liposomes containing celecoxib or plumbagin alone at the indicated dosage and compared to the same liposomes without any drug, P<0.001, two-way analysis of variance, and with negligible change in body weight over the treatment period as shown in the inset.
Figure 19A:
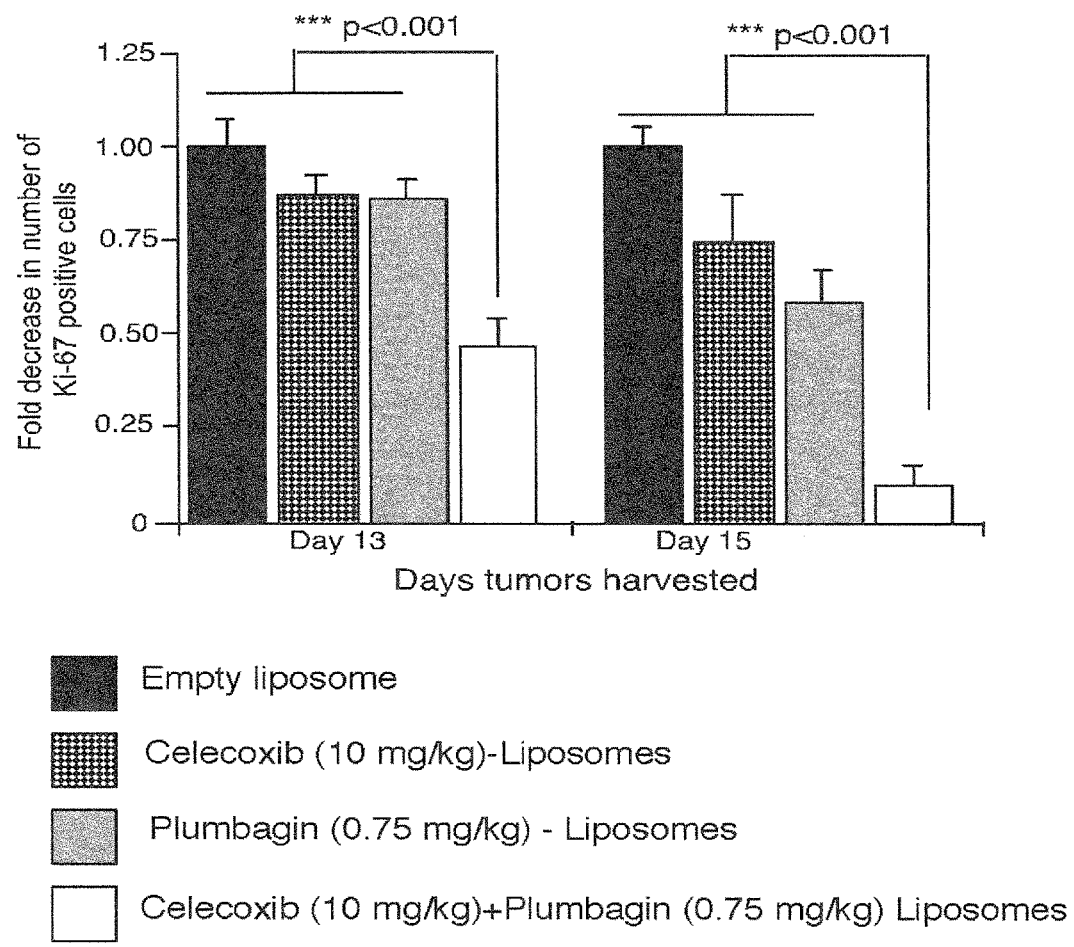
FIG. 19A is a graph showing a statistically significant reduction in proliferating cells at day 13 and 15 following administration liposomes containing both celecoxib and plumbagin at a 20:1 celecoxib:plumbagin ratio in the indicated dosage administered in saline to nude mice day 6 after injection of melanoma cells for xenograft tumor formation in nude mice, compared to empty liposomes of the same type and to the same liposomes containing only celecoxib, 15 mg/kg body weight or plumbagin, 0.75 mg/kg body weight; P<0.001, two-way analysis of variance.
Figure 19B:
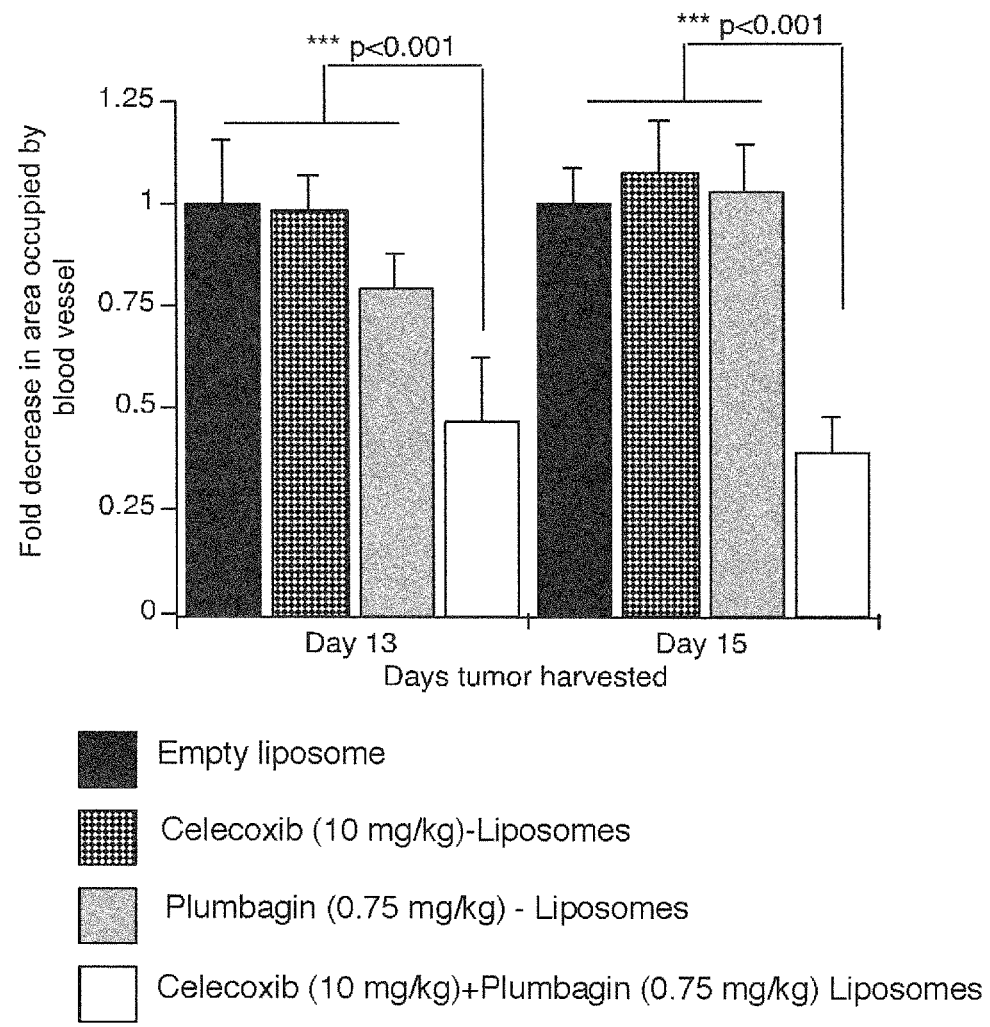
FIG. 19B is a graph showing a statistically significant reduction in vascular development at day 13 and 15 following administration liposomes containing both celecoxib and plumbagin at a 20:1 celecoxib:plumbagin ratio in the indicated dosage administered in saline to nude mice day 6 after injection of melanoma cells for xenograft tumor formation in nude mice, compared to empty liposomes of the same type and to the same liposomes containing only celecoxib, 15 mg/kg body weight or plumbagin, 0.75 mg/kg body weight; P<0.001, two-way analysis of variance.
Figure 19C:
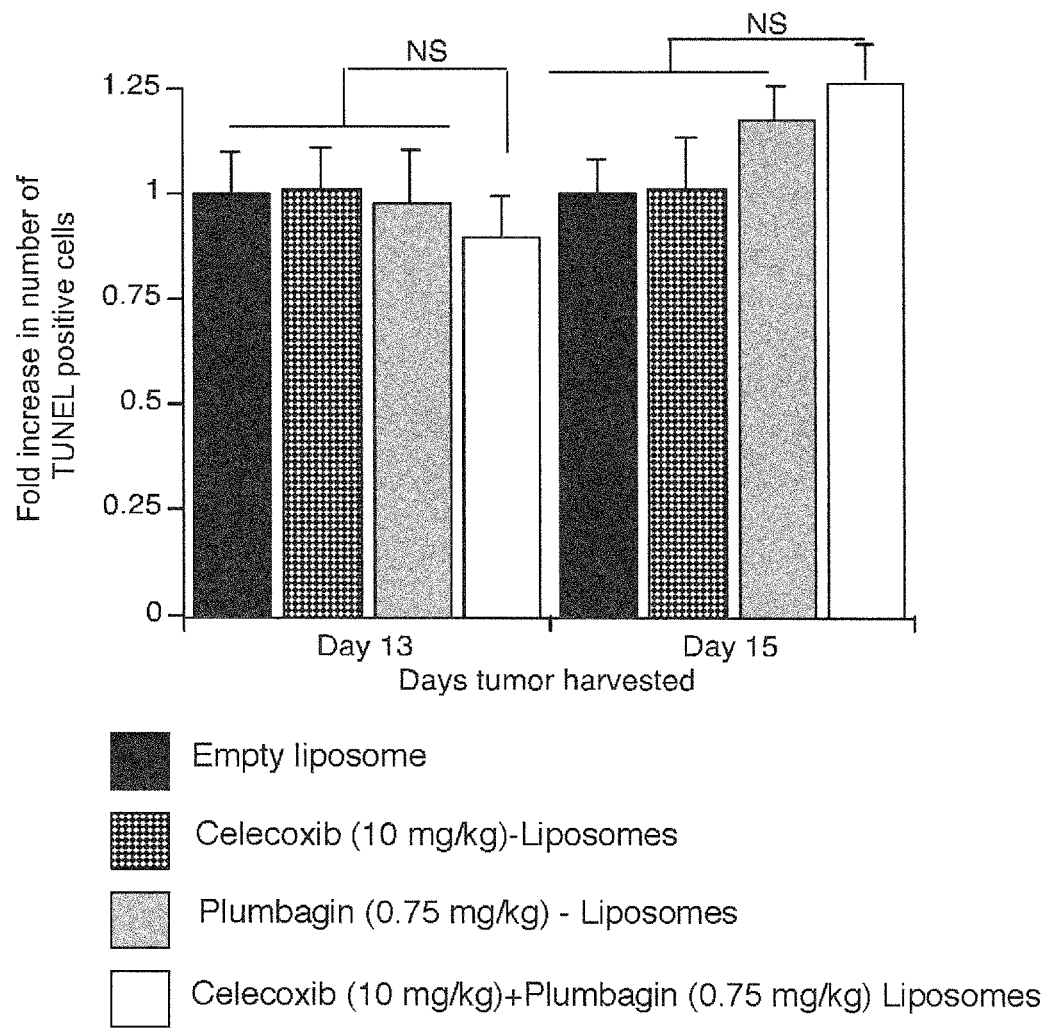
FIG. 19C is a graph showing no change was seen in tumor cells undergoing apoptosis at day 13 and 15 following administration liposomes containing both celecoxib and plumbagin at a 20:1 celecoxib:plumbagin ratio in the indicated dosage administered in saline to nude mice day 6 after injection of melanoma cells for xenograft tumor formation in nude mice, compared to empty liposomes of the same type and to the same liposomes containing only celecoxib, 15 mg/kg body weight or plumbagin, 0.75 mg/kg body weight; P<0.001, two-way analysis of variance.

To determine whether administration of liposomes containing both celecoxib and plumbagin would retard melanoma tumor development in a synergistic manner compared to nanoliposomes containing each individual drug, mice were injected subcutaneously with 1 million UACC 903 or 1205 Lu melanoma cells and tumors let develop for 7 days at which time fully vascularized tumors had developed. Animals were then treated by daily intravenous injections of liposomes containing both celecoxib and plumbagin containing the 1:20 plumbagin:celecoxib ratio of 15 mg/kg celecoxib+0.75 mg/kg plumbagin or 1:10 plumbagin:celecoxib ratio of 15 mg/kg celecoxib+1.5 mg/kg plumbagin based on body weight. Liposomes containing both celecoxib and plumbagin administered in water decreased tumor development by up to 65% for UACC 903 as shown in FIGS. 18A & 18B and up to 72% for 1205 Lu as shown in FIGS. 18C & 18D cells (P<0.001, two-way analysis of variance). Resuspending liposomes containing both celecoxib and plumbagin in either water, FIGS. 18C & 18D, or saline, FIGS. 18E & 18F, did not alter the tumor inhibitory efficacy leading to tumor inhibition of 50 to 72%. Liposomes containing both celecoxib and plumbagin treatment at either the 1:10 plumbagin:celecoxib ratio or 1:20 plumbagin:celecoxib ratio did not alter animal body weight, suggesting negligible toxicity as shown in FIGS. 18A to 18F; insets. FIGS. 18A and 18B, UACC 903 (1×10⁶) and FIGS. 18C, 18D, 18E and 18F, 1205 Lu (1×10⁶) melanoma cells were injected s.c. into left and right flanks near the rib cages of 4- to 6-week-old female nude mice. From day 6, mice were treated intravenously with nanoliposomes containing single agents (celecoxib 15 mg/kg body weight) and (plumbagin 0.75 or 1.5 mg/kg body weight), or combination of both (celecoxib 15 mg/kg body weight+plumbagin 0.75 or 1.5 mg/kg body weight). Empty liposomes in water or saline were used as a vehicle. Agents were delivered on alternate days for 3-4 wks. The sizes of developing tumors and body weights (inset) were measured at the time of each drug injection. The line graph presents tumor volume (mm³). Inset: body weight (g) measured during treatment. Data were obtained from duplicate experiments with three mice per group, containing two tumors per mouse. Each point represents average data obtained from six nude mice. Data represent means±SEM. *P<0.05, P<0.01, *P<0.001, two-way analysis of variance, followed by the post hoc test.

Liposomes Containing Both Celecoxib and Plumbagin Decreased Tumor Cells Proliferative Potential and Vascularization of Melanoma Tumors.

To identify the underlying mechanism by which liposomes containing both celecoxib and plumbagin inhibited melanoma tumor growth, an established analytic approach was used, see Stahl et al., Cancer Res. 2003 Jun. 1; 63(11): 2881-90 and Sharma et al., Clin Cancer Res. 2009 Mar. 1; 15(5):1674-85, which includes quantifying the rates of cell proliferation (using Ki-67 staining), apoptosis (using TUNEL staining) and tumor angiogenesis (using CD31 staining) occurring in time and size matched tumors treated with liposomes containing both celecoxib and plumbagin compared with control exposed animals. Nude mice bearing size and time matched xenograft tumors were treated with nanoliposomes containing single agents (celecoxib 15 mg/kg body weight) and (plumbagin 1.5 mg/kg body weight), or combination of both (celecoxib 15 mg/kg body weight+plumbagin 1.5 mg/kg body weight) starting day 6 until day 15. Empty liposomes in saline were used as a vehicle. Tumors were removed from mice on days 13 and 15, and tumor sections were immunostained for Ki-67 (FIG. 19A), CD31 (FIG. 19B) or TUNEL (FIG. 19C) to assess proliferation, vascular development and apoptosis, respectively. Images were quantified and plotted as fold difference in cells expressing Ki-67, area occupied by blood vessel or TUNEL-positive cells compared with controls. Data were obtained from three to four tumors, with four to five fields averaged per tumor. Data represent means±SEM. P<0.01, *P<0.01, not statistically significant. An analysis of variance, followed by a post hoc test was used. Size and time matched tumors at days 13 and 15 were compared to identify statistically quantifiable differences in cell proliferation, apoptosis or vascular development affected by liposomes containing both celecoxib and plumbagin treatment but not by nanoliposomes containing the individual drugs. At day 13, a statistically significant approximately 50% reduction in proliferating cells, FIG. 19A, and vascular development, FIG. 19B, was observed (P<0.001, two-way analysis of variance). In contrast no change was seen in tumor cells undergoing apoptosis, FIG. 19C. Similarly significant differences in cellular proliferation and vascular development were detected in all tumors compared with controls at day 15.

No significant changes in serum parameters indicative of major organ toxicity were observed as shown in Table I.

TABLE I

| Serum Parameters | EL | CL (15 mg/kg) | PL (1.5 mg/kg) | Celecoxib + Plumbagin (15 mg/kg + 1.5 mg/kg) |
|---|---|---|---|---|
| Glucose (90-192 mg/dL) | 220 ± 7.8 | 237 ± 13 | 207 ± 8.7 | 179 ± 52 |
| Blood Urea Nitrogen (18-29 mg/dL) | 20 ± 1.5 | 23 ± 2.0 | 21.3 ± 2.3 | 19 ± 5.1 |
| Creatinine (0.1-0.8 mg/dL) | ND | ND | ND | ND |
| Phosphate (6.1-10 mg/dL) | 11.9 ± 1.7 | 9.7 ± 0.3 | 9.5 ± 0.3 | 7.4 ± 5.1 |
| Total Protein (3.6-6.6 g/dL) | 6.3 ± 0.1 | 6.4 ± 0.2 | 5.9 ± 0.2 | 4.3 ± 5.1 |
| Calcium (5.9-9.4 mg/dL) | 10.8 ± 0.1 | 12 ± 0.2 | 10.2 ± 0.5 | 7.8 ± 2.4 |
| Globulin (2.5-4.6 g/dL) | 5.2 ± 0.1 | 5.1 ± 0.1 | 4.8 ± 0.05 | 3.7 ± 1.2 |
| ALT (SGPT) (28-132 U/L) | 110 ± 13 | 91 ± 4.7 | 103 ± 20 | 92.6 ± 12.4 |
| ALKP (62-209 U/L) | 123 ± 19 | 106 ± 15 | 94.6 ± 29 | 102.6 ± 30.2 |
| Total Bilirubin (0.1-0.9 mg/dL) | 0.3 ± 0.1 | 0.3 ± 0.0 | 0.3 ± 0.0 | 0.3 ± 0.1 |
| Cholesterol (36-96 mg/dL) | 88 ± 13 | 114 ± 14 | 81 ± 11 | 68 ± 35 |
| Triglycerides (55-144 mg/dL) | 110 ± 17 | 134 ± 23 | 139 ± 10 | 64 ± 11 |
| AST (SGOT) (59-247 U/L) | 164 ± 7.5 | 169 ± 11 | 224 ± 12 | 137 ± 9 |
| Amylase (1691-3615 U/L) | 2921 ± 123 | 2827 ± 48 | 3157 ± 91 | 2380 ± 509 |

Table I shows liposomes containing both celecoxib and plumbagin caused negligible toxicity at the concentrations examined. Levels of GLU (Glucose), BUN (Blood urea nitrogen), CREA (Creatinine), Phosphate, TP (Total Protein), CAL (Calcium), GLO (Globulin), ALT (Alanine aminotransferase), ALKP (Alkaline phosphatase), TBIL (Total bilirubin), CHOL (Total cholesterol), TRIG (Total triglyceride), AST (Aspartate aminotransferase) and AMY (Amylase) were analyzed in blood collected from animals treated with liposomes containing single agents (celecoxib 15 mg/kg body weight) and (plumbagin 1.5 mg/kg body weight), or combination of both (celecoxib 15 mg/kg body weight+plumbagin 1.5 mg/kg body weight) to measure effects on major organ related toxicity. Values in brackets represent the normal serum range of each for nude mice; values, mean±S.E.

Analysis of hematoxylin & eosin (H & E) stained tissue sections comparing control mice with mice treated with liposomes containing both celecoxib and plumbagin showed no changes in cellular morphology or architecture of liver, heart, lung, kidney, spleen and intestine. These data indicate that liposomes containing both celecoxib and plumbagin inhibits xenografted melanoma tumor development without significant organ related toxicity.

Liposomes Containing Both Celecoxib and Plumbagin Inhibited the Activity of Cyclins and STAT3 to Retard Melanoma Tumor Development.

Figure 20A:
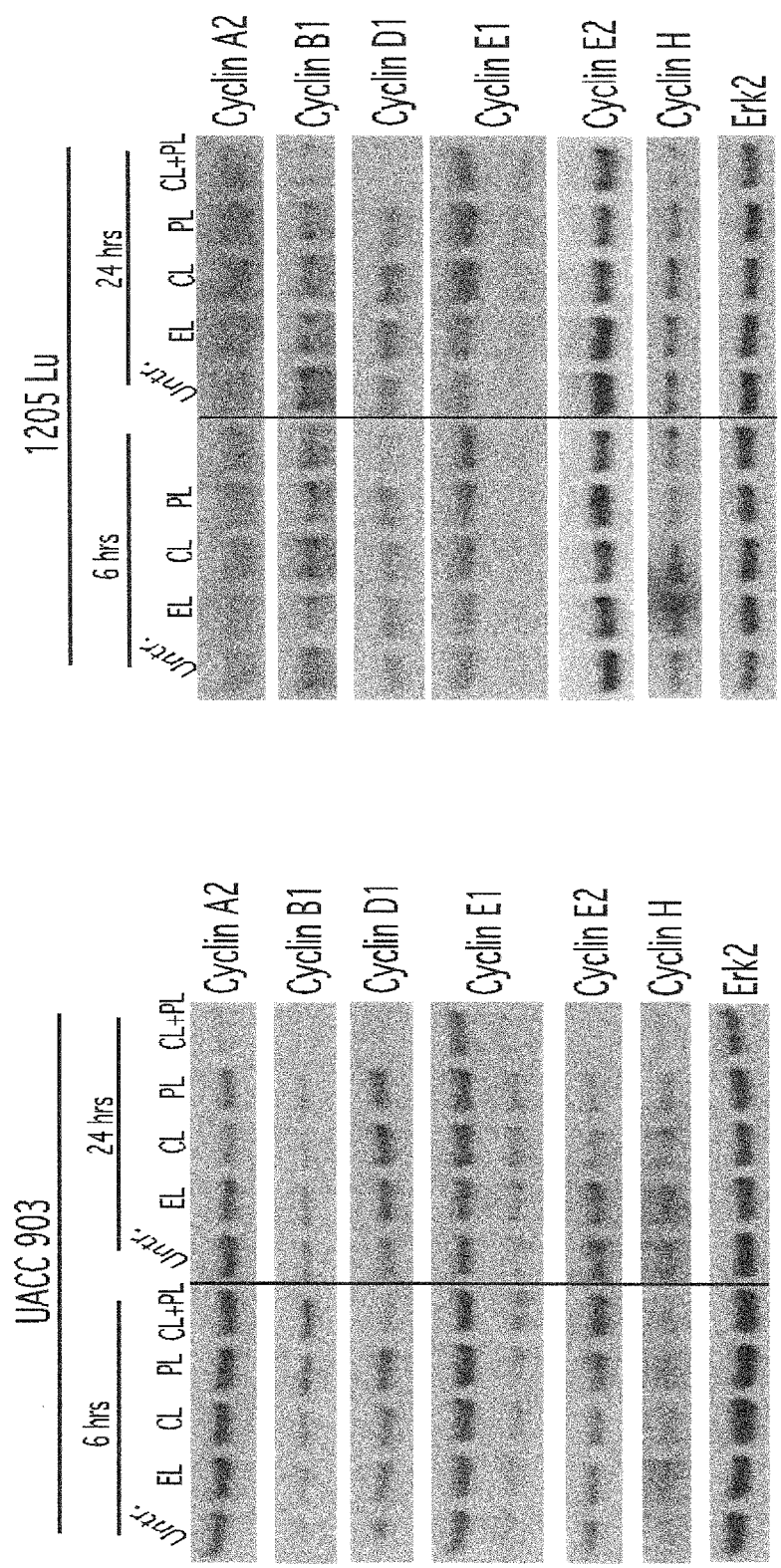
FIG. 20A is an image of Western blots performed to measure changes in protein expression of cyclins in cell lysates from UACC 903 or 1205 Lu melanoma cells treated with empty control liposomes, 100 µmol/L celecoxib liposomes, 5 µmol/L plumbagin liposomes, or liposomes containing both celecoxib and plumbagin (containing 100 µmol/L, celecoxib+5 µmol/L plumbagin) for 6 or 24 hours and showing that cyclins A2, B1, D1 and H were decreased in both UACC 903 and 1205 Lu melanoma cells by treatment with liposomes containing both celecoxib and plumbagin.
Figure 20B:
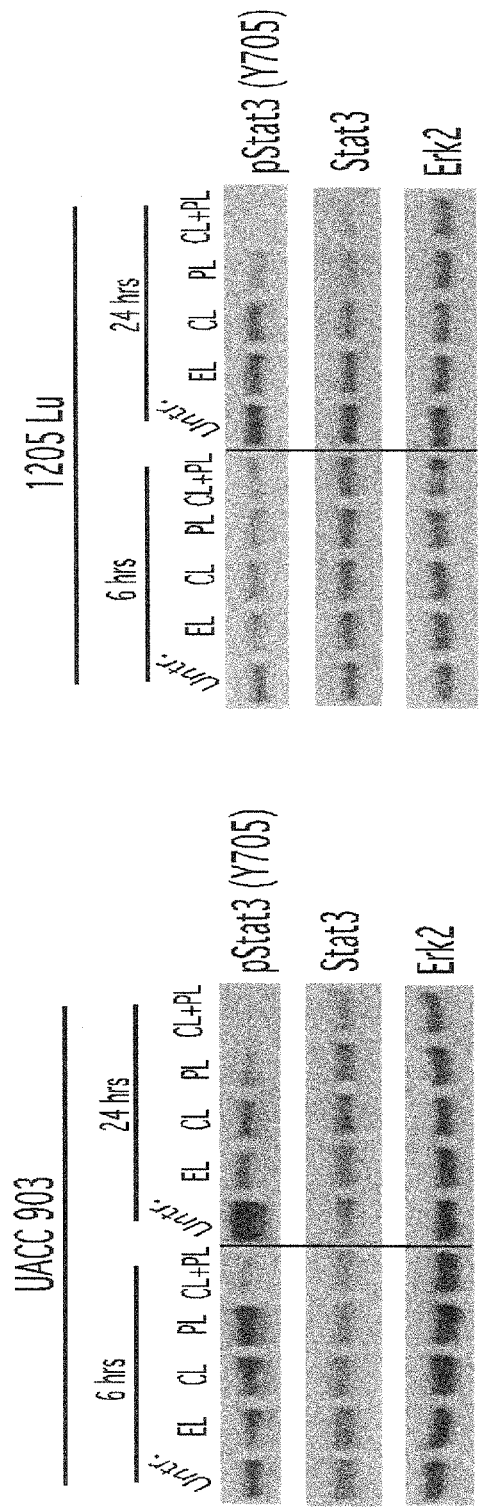
FIG. 20B is an image of Western blots performed to measure changes in protein expression of pStat3 in cell lysates from UACC 903 or 1205 Lu melanoma cells treated with empty control liposomes, 100 µmol/L celecoxib liposomes, 5 µmol/L plumbagin liposomes, or liposomes containing both celecoxib and plumbagin (containing 100 µmol/L celecoxib+5 µmol/L plumbagin) for 6 or 24 hours and showing that pStat3 was decreased in both UACC 903 and 1205 Lu melanoma cells by treatment with liposomes containing both celecoxib and plumbagin.
Figure 20C:
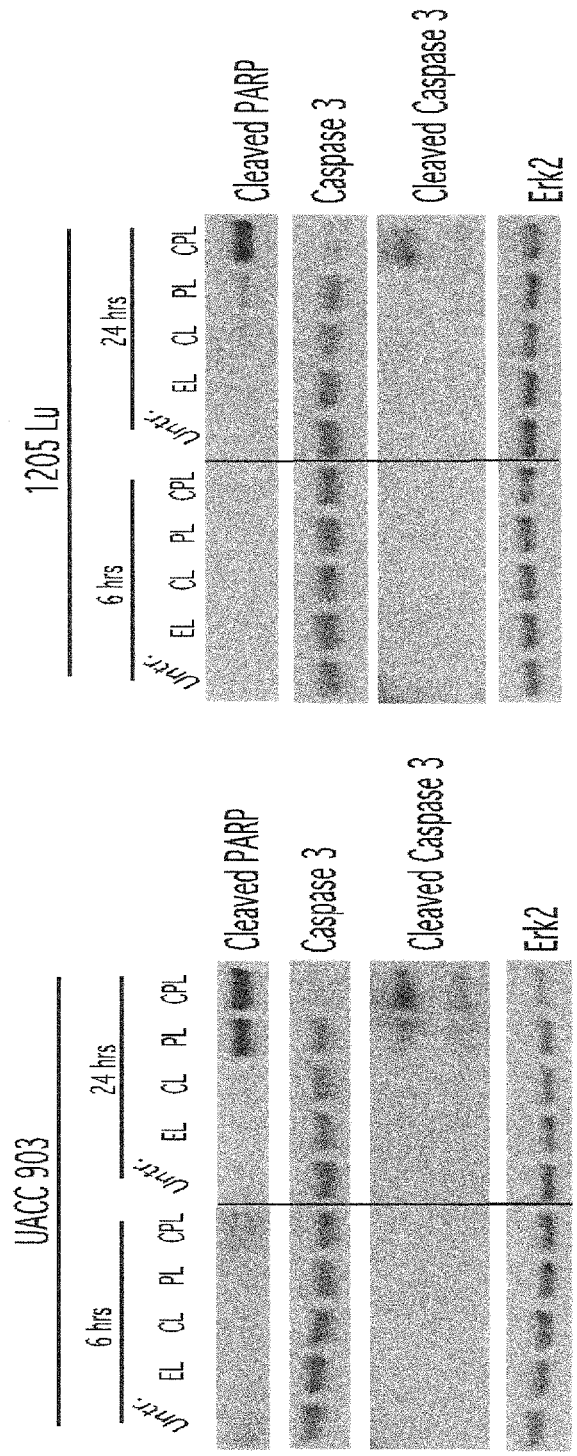
FIG. 20C is an image of Western blots performed to measure changes in protein expression of apoptotic markers in cell lysates from UACC 903 or 1205 Lu melanoma cells treated with empty control liposomes, 100 µmol/L celecoxib liposomes, 5 µmol/L plumbagin liposomes, or liposomes containing both celecoxib and plumbagin (containing 100 µmol/L celecoxib+5 µmol/L plumbagin) for 6 or 24 hours and showing that cleaved PARP and cleaved caspase 3 were increased in both UACC 903 and 1205 Lu melanoma cells by treatment with liposomes containing both celecoxib and plumbagin.
Figure 21A:
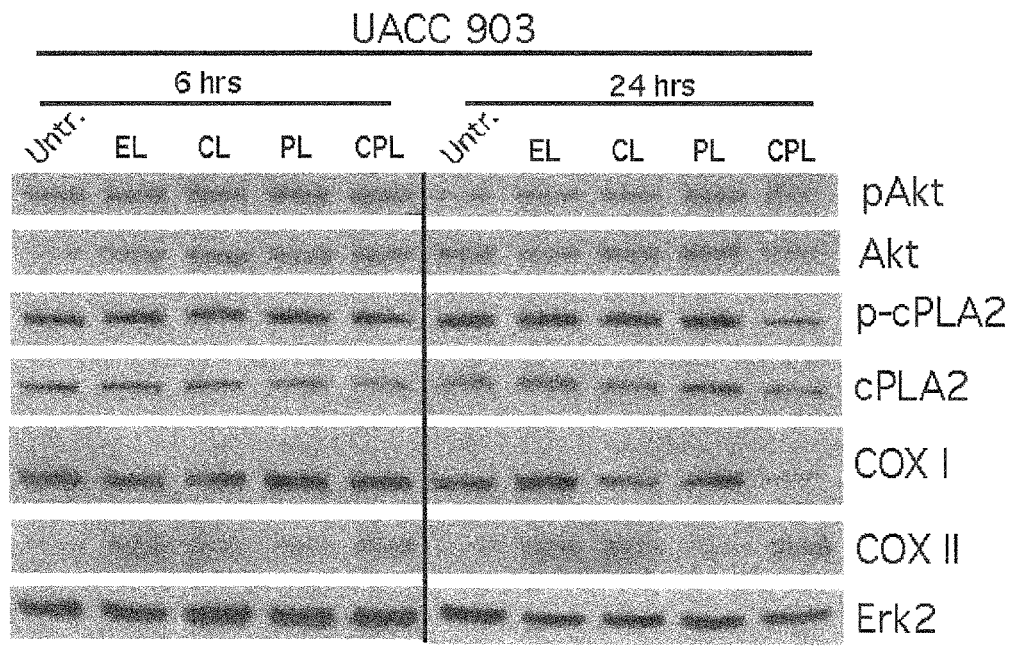
FIG. 21A is an image of Western blots performed to measure changes in protein expression of various indicated proteins in cell lysates from UACC 903 cells treated with empty control liposomes, 100 µmol/L celecoxib liposomes, 5 µmol/L plumbagin liposomes, or liposomes containing both celecoxib and plumbagin (containing 100 µmol/L celecoxib+5 µmol/L, plumbagin) for 6 or 24 hours and showing that Akt or cytosolic PLA2 were relatively unchanged by treatment with liposomes containing both celecoxib and plumbagin.
Figure 21B:
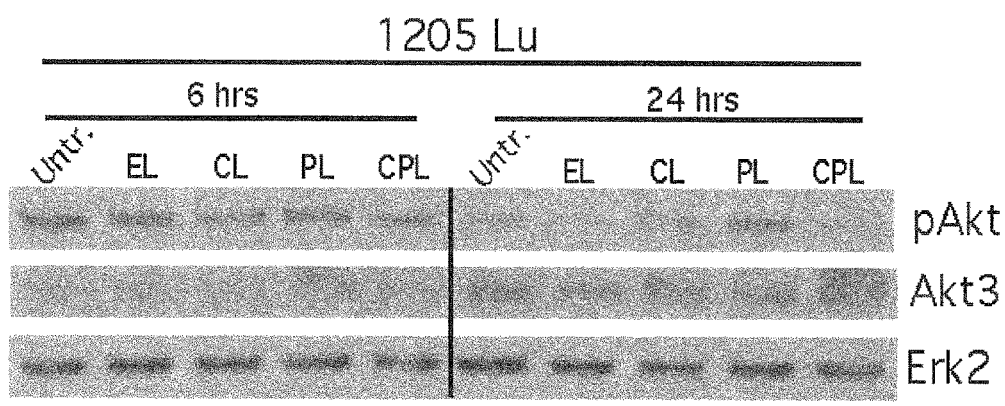
FIG. 21B is an image of Western blots performed to measure changes in protein expression of various indicated proteins in cell lysates from 1205 Lu cells treated with empty control liposomes, 100 µmol/L celecoxib liposomes, 5 µmol/L plumbagin liposomes, or liposomes containing both celecoxib and plumbagin (containing 100 µmol/L celecoxib+5 µmol/L plumbagin) for 6 or 24 hours and showing that Akt or cytosolic PLA2 were relatively unchanged by treatment with liposomes containing both celecoxib and plumbagin.

To identify the mechanism through which nanoliposomes containing both celecoxib and plumbagin decreased melanoma tumor development more effectively that either celecoxib or plumbagin alone, cells were treated with nanoliposomes containing each agent alone or combined. Western blotting was performed to measure changes in protein expression of (FIG. 20A) cyclins, (FIG. 20B) STAT3 signaling, or (FIG. 20C) apoptotic markers. Cell lysates from UACC 903 or 1205 Lu melanoma cells treated with empty control liposomes, 100 µmol/L celecoxib liposomes, 5 µmol/L plumbagin liposomes, or liposomes containing both celecoxib and plumbagin (containing 100 µmol/L celecoxib+5 µmol/L plumbagin) for 6 or 24 hours followed by harvesting in RIPA lysis buffer containing Halt Protease & Phosphatase Inhibitor Cocktail (Thermo Scientific, Rockford, Ill.). Blots were probed with antibodies according to each supplier's recommendations: antibodies to Akt(pan) (11E7) (#4685), Akt3 (#3788), Cleaved PARP (Asp 214) (#9541), pStat3 (Y705) (#9145), Stat3 (#4904), cyclin H (#2927), cyclin B1 (#4138), caspase 3 (#9662), cyclin A2 (#4656), cyclin E1 (#4129), cyclin E2 (#4132), CPLA2 (#2832), and pCPLA2 (S505) (#2831) from Cell Signaling Technology (Danvers, Mass.); cyclin D1 (sc-718), Erk2 (sc-1647), p21 (sc-756), p27 (sc-528), COXI (sc-1752), COXII (sc-1745) and secondary antibodies conjugated with horseradish peroxidase from Santa Cruz Biotechnology (Santa Cruz, Calif.). Immunoblots were developed using the enhanced chemiluminescence (ECL) detection system (Thermo Fisher Scientific, Rockford, Ill.) or Supersignal West Femto Chemiluminescent Substrate (Thermo Fisher Scientific, Rockford, Ill.). FIGS. 20A-C shows results of Western blots using proteins from UACC 903 or 1205 Lu melanoma cells treated with empty control liposome, celecoxib liposome (100 uM), plumbagin liposome (5 uM), or liposomes containing both celecoxib and plumbagin (100 uM celecoxib+5 uM plumbagin) for 24 hours. FIGS. 21A and 21B show liposomes containing both celecoxib and plumbagin had no effect Akt or CPLA2 signaling. Western blotting was performed on UACC 903, FIG. 21A, or 1205 Lu, FIG. 21B, melanoma cell lysates from cells treated with empty control liposome, celecoxib liposome (100 µmol/L), plumbagin liposome (5 µmol/L), or liposomes containing both celecoxib and plumbagin (100 µmol/L celecoxib, 5 µmol/L plumbagin) for 24 hours. Liposomes containing both celecoxib and plumbagin had negligible effects on numerous proteins including Akt shown in FIGS. 21A and 21B, or CPLA2 signaling, as shown in FIG. 21A; however, it did consistently decrease the levels of Cox-2 as shown in FIG.

21A, several cyclins as shown in FIG. 20A and pStat3, as shown in FIG. 20B, in both UACC 903 and 1205 Lu cells. In both melanoma cell lines cyclins A2, B1, D1 and H were decreased. In addition to reductions of these cyclins, in UACC 903 cells Cyclin E1 and E2 were also decreased. Cyclins are key to the functioning of the cyclin-cyclin dependent kinase complex in melanoma cells. Reductions in the levels of these proteins was more prominent following treatment with liposomes containing both celecoxib and plumbagin than celecoxib or plumbagin alone, thus affecting cell proliferation. Consistent with increased cell death mediated by liposomes containing both celecoxib and plumbagin, treatment with liposomes containing both celecoxib and plumbagin led to increased levels of cleaved PARP and caspase 3 compared to exposure to nanoliposomes containing celecoxib or plumbagin alone as shown in FIG. 20C. Thus, the mechanism leading to reduction in the proliferative potential of melanoma cells following treatment with liposomes containing both celecoxib and plumbagin appeared to be mediated through reductions in the levels of key cyclins. Apoptosis appears to be mediated through decreased levels of active STAT3.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A pharmaceutical composition, comprising: plumbagin and celecoxib in a synergistic ratio in the range of 1:7.5-1:20 effective to decrease viability of melanoma cells; and a pharmaceutically acceptable carrier.

2. The pharmaceutical composition of claim 1, wherein the pharmaceutically acceptable carrier comprises liposomes.

3. The pharmaceutical composition of claim 2, wherein the liposomes have an average particle size in the range of 1 nm-500 nm.

4. The pharmaceutical composition of claim 1, wherein the plumbagin is present in a concentration in the range of 0.1 micromolar-100 millimolar and the celecoxib is present in a concentration in the range of 0.1 micromolar-100 millimolar.

5. The pharmaceutical composition of claim 2, wherein the liposomes comprise at least one polyethylene glycol modified neutral lipid, wherein the amount of polyethylene glycol modified neutral lipid is an amount in the range of 2.5-30 molar percent, inclusive, of total lipids in the liposomes; and one or more anionic, cationic or neutral lipids in an amount in the range of 70-97.5, inclusive, molar percent of total lipids in the liposomes.

6. The pharmaceutical composition of claim 2, wherein the liposomes comprise at least one polyethylene glycol modified neutral lipid, wherein the amount of polyethylene glycol modified neutral lipid is an amount in the range of 5-20 molar percent, inclusive, of total lipids in the liposomes; and one or more anionic, cationic or neutral lipids in an amount in the range of 80-95, inclusive, molar percent of total lipids in the liposomes.

7. A method of treating melanoma in a subject in need thereof, comprising: administering, concurrently or sequentially, a therapeutically effective amount of plumbagin and celecoxib in a synergistic ratio in the range of 1:7.5-1:20 to the subject.

8. The method of treating melanoma of claim 7, wherein administering the therapeutically effective amount of plumbagin and celecoxib to the subject comprises administering liposomes containing plumbagin and/or liposomes containing celecoxib.

9. The method of treating melanoma of claim 8, wherein the liposomes have an average particle size in the range of 1 nm-500 nm.

10. The method of treating melanoma of claim 7, wherein the plumbagin is administered in a concentration in the range of 0.1 micromolar-100 millimolar and the celecoxib is administered in a concentration in the range of 0.1 micromolar-100 millimolar.

11. The method of treating melanoma of claim 7, wherein the subject is human.

12. The method of treating melanoma of claim 7, wherein the subject has malignant melanoma.

13. The method of treating melanoma of claim 7, wherein the melanoma is characterized by abnormal activation of COX-2 and STAT3.

14. The method of treating melanoma of claim 7, further comprising assay of COX-2 and/or STAT3 to detect abnormal activation of COX-2 and/or STAT3 in a sample obtained from the subject containing melanoma cells.

15. The method of treating melanoma of claim 7, further comprising administration of an adjunct anti-cancer treatment.

16. A commercial package, comprising: a pharmaceutical composition comprising: plumbagin and celecoxib in a synergistic ratio in the range of 1:7.5-1:20 effective to decrease viability of melanoma cells; and a pharmaceutically acceptable carrier.

* * * * *